United States Patent
Lim et al.

(10) Patent No.: US 11,641,879 B2
(45) Date of Patent: May 9, 2023

(54) AEROSOL GENERATION DEVICE AND CONTROL METHOD FOR AEROSOL GENERATION DEVICE

(71) Applicant: KT&G CORPORATION, Daejeon (KR)

(72) Inventors: Hun Il Lim, Seoul (KR); Jung Ho Han, Daejeon (KR); Jong Sub Lee, Seongnam-si (KR); Dae Nam Han, Daejeon (KR); Jin Young Yoon, Seoul (KR); Young Lea Kim, Seoul (KR); Jang Uk Lee, Seoul (KR); Ji Soo Jang, Seoul (KR); Du Jin Park, Seoul (KR); Seong Won Yoon, Yongin-si (KR); Wang Seop Lim, Anyang-si (KR); Moon Bong Lee, Seoul (KR); Soung Ho Ju, Daejeon (KR)

(73) Assignee: KT&G CORPORATION, Daejeon (KR)

( * ) Notice: Subject to any disclaimer, the term of this patent is extended or adjusted under 35 U.S.C. 154(b) by 191 days.

(21) Appl. No.: 16/635,599

(22) PCT Filed: Aug. 9, 2018

(86) PCT No.: PCT/KR2018/009100
§ 371 (c)(1),
(2) Date: Jan. 31, 2020

(87) PCT Pub. No.: WO2019/031877
PCT Pub. Date: Feb. 14, 2019

(65) Prior Publication Data
US 2020/0237005 A1    Jul. 30, 2020

(30) Foreign Application Priority Data

Aug. 9, 2017  (KR) .................... 10-2017-0100888
Feb. 14, 2018 (KR) .................... 10-2018-0018693

(51) Int. Cl.
*A24F 40/40* (2020.01)
*A24F 40/90* (2020.01)
(Continued)

(52) U.S. Cl.
CPC .............. *A24F 40/40* (2020.01); *A24F 40/46* (2020.01); *A24F 40/51* (2020.01); *A24F 40/57* (2020.01);
(Continued)

(58) Field of Classification Search
CPC ........... A24F 40/40; A24F 40/50; A24F 40/90
See application file for complete search history.

(56) References Cited

U.S. PATENT DOCUMENTS 2,638,904 A    5/1953  Mitchell
4,585,014 A    4/1986  Fry
(Continued)

FOREIGN PATENT DOCUMENTS

CA    2 973 143 A1    8/2016
CA    2975654 A1      8/2016
(Continued)

OTHER PUBLICATIONS

Office Action dated Sep. 24, 2020 in Korean Application No. 10-2018-0012456.
(Continued)

*Primary Examiner* — Anthony Calandra
(74) *Attorney, Agent, or Firm* — Sughrue Mion, PLLC

(57) ABSTRACT

Provided is an aerosol generation device including: a power supplier comprising a first battery and a second battery; a controller; and a heater, wherein the controller is configured to control the power supplier to operate according to one of a first mode in which power is supplied to the heater by using the first battery and a second mode in which power is supplied to the heater by using the second battery, and
(Continued)

control the power supplier to supply greater power in the first mode than in the second mode.

16 Claims, 27 Drawing Sheets

(51) Int. Cl.
    *A24F 40/46*      (2020.01)
    *A24F 40/51*      (2020.01)
    *A24F 40/60*      (2020.01)
    *A24F 40/85*      (2020.01)
    *A24F 40/65*      (2020.01)
    *A24F 40/57*      (2020.01)
    *A24F 40/20*      (2020.01)

(52) U.S. Cl.
    CPC .............. *A24F 40/60* (2020.01); *A24F 40/65* (2020.01); *A24F 40/85* (2020.01); *A24F 40/20* (2020.01); *A24F 40/90* (2020.01)

(56) References Cited

U.S. PATENT DOCUMENTS

| | | |
|---|---|---|
| 4,637,407 A | 1/1987 | Bonanno et al. |
| 5,144,962 A | 9/1992 | Counts et al. |
| 5,240,012 A | 8/1993 | Ehrman et al. |
| 5,249,586 A | 10/1993 | Morgan et al. |
| 5,388,594 A | 2/1995 | Counts et al. |
| 5,465,738 A | 11/1995 | Rowland |
| 5,479,948 A | 1/1996 | Counts et al. |
| 5,499,636 A | 3/1996 | Baggett, Jr. et al. |
| 5,591,368 A | 1/1997 | Fleischhauer et al. |
| 5,666,977 A | 9/1997 | Higgins et al. |
| 5,878,752 A | 3/1999 | Adams et al. |
| 5,967,148 A | 10/1999 | Harris et al. |
| 6,026,820 A | 2/2000 | Baggett, Jr. et al. |
| 6,040,560 A | 3/2000 | Fleischhauer et al. |
| 6,053,176 A | 4/2000 | Adams et al. |
| 6,418,938 B1 | 7/2002 | Fleischhauer et al. |
| 6,532,965 B1 | 3/2003 | Abhulimen et al. |
| 6,615,840 B1 | 9/2003 | Fournier et al. |
| 6,810,883 B2 | 11/2004 | Felter et al. |
| 7,861,726 B1 | 4/2011 | Lukasavitz |
| 8,375,959 B2 | 2/2013 | Dittrich et al. |
| 8,419,085 B2 | 4/2013 | Kim et al. |
| 8,752,545 B2 | 6/2014 | Buchberger |
| 8,851,081 B2 | 10/2014 | Fernando et al. |
| 8,973,587 B2 | 3/2015 | Liu |
| 9,078,472 B2 | 7/2015 | Liu |
| 9,078,473 B2 | 7/2015 | Worm et al. |
| 9,185,939 B2 | 11/2015 | Jarriault et al. |
| 9,220,304 B2 | 12/2015 | Greim |
| 9,271,528 B2 | 3/2016 | Liu |
| 9,320,299 B2 | 4/2016 | Hearn et al. |
| 9,423,152 B2 | 8/2016 | Ampolini et al. |
| 9,427,023 B2 | 8/2016 | Liu |
| 9,497,991 B2 | 11/2016 | Besso et al. |
| 9,499,332 B2 | 11/2016 | Fernando et al. |
| 9,504,279 B2 | 11/2016 | Chen |
| 9,516,899 B2 | 12/2016 | Plojoux et al. |
| 9,560,883 B2 | 2/2017 | Hawes |
| 9,603,388 B2 | 3/2017 | Fernando et al. |
| 9,655,383 B2 | 5/2017 | Holzherr et al. |
| 9,693,587 B2 | 7/2017 | Plojoux et al. |
| 9,723,871 B2 | 8/2017 | Xiang |
| 9,795,166 B2 | 10/2017 | Liu |
| 9,814,263 B2 | 11/2017 | Cochand et al. |
| 9,854,841 B2 | 1/2018 | Ampolini et al. |
| 9,854,845 B2 | 1/2018 | Plojoux et al. |
| 9,894,934 B2 | 2/2018 | Li et al. |
| 9,918,494 B2 | 3/2018 | Mironov et al. |
| 9,955,724 B2 | 5/2018 | Lord |
| 9,986,760 B2 | 6/2018 | Macko et al. |
| 9,999,247 B2 | 6/2018 | Ruscio et al. |
| 10,015,990 B2 | 7/2018 | Mironov |
| 10,031,183 B2 | 7/2018 | Novak, III et al. |
| 10,070,667 B2 | 9/2018 | Lord et al. |
| 10,104,911 B2 | 10/2018 | Thorens et al. |
| 10,130,780 B2 | 11/2018 | Talon |
| 10,136,673 B2 | 11/2018 | Mironov |
| 10,159,283 B2 | 12/2018 | Mironov |
| 10,194,697 B2 | 2/2019 | Fernando et al. |
| 10,299,513 B2 | 5/2019 | Perez et al. |
| 10,368,584 B2 | 8/2019 | Fernando et al. |
| 10,439,419 B2 | 10/2019 | Bernauer et al. |
| 10,440,987 B2 | 10/2019 | Zeng et al. |
| 10,448,670 B2 | 10/2019 | Talon et al. |
| 10,492,542 B1 | 12/2019 | Worm et al. |
| 10,548,350 B2 | 2/2020 | Greim et al. |
| 10,555,553 B2 | 2/2020 | Binassi et al. |
| 10,555,555 B2 | 2/2020 | Fernando et al. |
| 10,588,351 B2 | 3/2020 | Ricketts |
| 10,617,149 B2 | 4/2020 | Malgat et al. |
| 10,645,971 B2 | 5/2020 | Zitzke |
| 10,667,329 B2 | 5/2020 | Bernauer et al. |
| 10,668,058 B2 | 6/2020 | Rose et al. |
| 10,716,329 B2 | 7/2020 | Matsumoto et al. |
| 10,757,975 B2 | 9/2020 | Batista et al. |
| 10,813,174 B2 | 10/2020 | Schneider et al. |
| 10,869,503 B2 | 12/2020 | Yamada et al. |
| 10,881,131 B2 | 1/2021 | Matsumoto et al. |
| 10,881,137 B2 | 1/2021 | Suzuki et al. |
| 10,881,143 B2 | 1/2021 | Suzuki et al. |
| 11,039,642 B2 | 6/2021 | Zuber et al. |
| 11,147,316 B2 | 10/2021 | Farine et al. |
| 11,445,576 B2 | 9/2022 | Zinovik et al. |
| 2004/0261802 A1 | 12/2004 | Griffin et al. |
| 2005/0045198 A1 | 3/2005 | Larson et al. |
| 2005/0172976 A1 | 8/2005 | Newman et al. |
| 2006/0030214 A1 | 2/2006 | Katou et al. |
| 2008/0001052 A1 | 1/2008 | Kalous et al. |
| 2010/0001538 A1 | 1/2010 | Kim et al. |
| 2010/0024834 A1 | 2/2010 | Oglesby et al. |
| 2010/0307518 A1 | 9/2010 | Wang |
| 2010/0313901 A1* | 12/2010 | Fernando .............. H02J 7/0044 131/330 |
| 2011/0155151 A1 | 6/2011 | Newman et al. |
| 2011/0209717 A1 | 9/2011 | Han |
| 2011/0226236 A1 | 9/2011 | Buchberger |
| 2011/0265806 A1 | 11/2011 | Alarcon et al. |
| 2011/0290248 A1 | 12/2011 | Schennum |
| 2011/0290269 A1 | 12/2011 | Shimizu |
| 2012/0048266 A1 | 3/2012 | Alelov |
| 2012/0247494 A1 | 10/2012 | Oglesby et al. |
| 2013/0014772 A1 | 1/2013 | Liu |
| 2013/0037041 A1 | 2/2013 | Worm et al. |
| 2013/0074857 A1 | 3/2013 | Buchberger |
| 2013/0213419 A1 | 8/2013 | Tucker et al. |
| 2013/0284192 A1 | 10/2013 | Peleg et al. |
| 2013/0319439 A1 | 12/2013 | Gorelick et al. |
| 2013/0319440 A1* | 12/2013 | Capuano .............. A61M 15/06 131/329 |
| 2013/0340775 A1 | 12/2013 | Juster et al. |
| 2014/0014125 A1 | 1/2014 | Fernando et al. |
| 2014/0020698 A1 | 1/2014 | Fiebelkorn |
| 2014/0096782 A1 | 4/2014 | Ampolini et al. |
| 2014/0246035 A1 | 4/2014 | Minskoff et al. |
| 2014/0116455 A1 | 5/2014 | Youn |
| 2014/0299137 A1 | 10/2014 | Kieckbusch et al. |
| 2014/0301721 A1 | 10/2014 | Ruscio et al. |
| 2014/0305448 A1 | 10/2014 | Zuber et al. |
| 2014/0318559 A1 | 10/2014 | Thorens et al. |
| 2014/0345634 A1 | 11/2014 | Zuber et al. |
| 2014/0363145 A1 | 12/2014 | Plojoux et al. |
| 2015/0007838 A1 | 1/2015 | Fernando et al. |
| 2015/0013696 A1 | 1/2015 | Plojoux et al. |
| 2015/0020832 A1 | 1/2015 | Greim et al. |
| 2015/0024355 A1 | 1/2015 | Ghofrani et al. |
| 2015/0027474 A1 | 1/2015 | Zuber et al. |
| 2015/0272211 A1 | 1/2015 | Chung |
| 2015/0100441 A1 | 4/2015 | Alarcon et al. |
| 2015/0136124 A1 | 5/2015 | Aronie et al. |
| 2015/0136154 A1 | 5/2015 | Mitrev et al. |

(56) References Cited

U.S. PATENT DOCUMENTS

| | | |
|---|---|---|
| 2015/0208725 A1 | 7/2015 | Tsai |
| 2015/0208730 A1 | 7/2015 | Li et al. |
| 2015/0245654 A1 | 9/2015 | Memari et al. |
| 2015/0245666 A1 | 9/2015 | Memari et al. |
| 2015/0257445 A1 | 9/2015 | Henry, Jr. et al. |
| 2016/0150824 A1 | 6/2016 | Memari et al. |
| 2016/0235121 A1 | 8/2016 | Rogan et al. |
| 2016/0270437 A1 | 9/2016 | Nappi |
| 2016/0286861 A1 | 10/2016 | Liu |
| 2016/0302488 A1 | 10/2016 | Fernando et al. |
| 2016/0331032 A1 | 11/2016 | Malgat et al. |
| 2016/0345629 A1 | 12/2016 | Mironov |
| 2016/0366946 A1 | 12/2016 | Murison et al. |
| 2016/0374402 A1 | 12/2016 | Fernando et al. |
| 2017/0006916 A1 | 1/2017 | Liu |
| 2017/0006919 A1 | 1/2017 | Liu |
| 2017/0027229 A1 | 2/2017 | Cameron |
| 2017/0027234 A1 | 2/2017 | Farine et al. |
| 2017/0042243 A1 | 2/2017 | Plojoux et al. |
| 2017/0055580 A1 | 3/2017 | Blandino et al. |
| 2017/0065002 A1 | 3/2017 | Fernando et al. |
| 2017/0071251 A1 | 3/2017 | Goch |
| 2017/0095006 A1 | 6/2017 | Egoyants et al. |
| 2017/0150757 A1 | 6/2017 | Worm et al. |
| 2017/0164659 A1 | 6/2017 | Schneider et al. |
| 2017/0172214 A1 | 6/2017 | Li et al. |
| 2017/0172215 A1 | 6/2017 | Li et al. |
| 2017/0188634 A1 | 7/2017 | Plojoux et al. |
| 2017/0295844 A1 | 10/2017 | Thevenaz et al. |
| 2018/0070634 A1* | 3/2018 | Sur .................. H05B 1/0244 |
| 2018/0177234 A1 | 6/2018 | Lee |
| 2018/0206556 A1 | 7/2018 | Thorens et al. |
| 2018/0235283 A1 | 8/2018 | Zuber et al. |
| 2019/0014826 A1 | 1/2019 | Thorens et al. |
| 2019/0075849 A1 | 3/2019 | Hawes |
| 2019/0320719 A1 | 10/2019 | Liu et al. |
| 2019/0364975 A1 | 12/2019 | Fernando et al. |
| 2020/0006950 A1 | 1/2020 | Holzherr |
| 2020/0305508 A1 | 1/2020 | Talon |
| 2020/0120983 A1 | 4/2020 | Chen |
| 2020/0232766 A1 | 7/2020 | Flick |
| 2020/0352224 A1 | 11/2020 | Plojoux et al. |
| 2020/0413495 A1 | 12/2020 | Schneider et al. |
| 2021/0000182 A1 | 1/2021 | Ruscio et al. |
| 2021/0106051 A1 | 4/2021 | Han et al. |
| 2021/0120875 A1 | 4/2021 | Mironov |

FOREIGN PATENT DOCUMENTS

| | | |
|---|---|---|
| CH | 310239 A | 12/1955 |
| CN | 2146758 Y | 11/1993 |
| CN | 1102964 A | 5/1995 |
| CN | 1122213 A | 5/1996 |
| CN | 1190335 A | 8/1998 |
| CN | 1209731 A | 3/1999 |
| CN | 2857109 Y | 1/2007 |
| CN | 1973706 A | 6/2007 |
| CN | 101043827 A | 9/2007 |
| CN | 101444335 A | 6/2009 |
| CN | 201491717 U | 6/2010 |
| CN | 102006790 A | 4/2011 |
| CN | 102109393 A | 6/2011 |
| CN | 102326869 A | 1/2012 |
| CN | 102438470 A | 5/2012 |
| CN | 202407082 U | 9/2012 |
| CN | 202774134 U | 3/2013 |
| CN | 103096741 A | 5/2013 |
| CN | 103281920 A | 9/2013 |
| CN | 103338665 A | 10/2013 |
| CN | 103622162 A | 3/2014 |
| CN | 203457802 U | 3/2014 |
| CN | 203575658 U | 5/2014 |
| CN | 103859606 A | 6/2014 |
| CN | 203633505 U | 6/2014 |
| CN | 203646503 U | 6/2014 |
| CN | 103929988 A | 7/2014 |
| CN | 203689071 U | 7/2014 |
| CN | 203692545 U | 7/2014 |
| CN | 103974638 A | 8/2014 |
| CN | 103974640 A | 8/2014 |
| CN | 103987286 A | 8/2014 |
| CN | 103997921 A | 8/2014 |
| CN | 103997922 A | 8/2014 |
| CN | 203789137 U | 8/2014 |
| CN | 104023568 A | 9/2014 |
| CN | 104023574 A | 9/2014 |
| CN | 104039183 A | 9/2014 |
| CN | 203814592 U | 9/2014 |
| CN | 104095295 A | 10/2014 |
| CN | 104106842 A | 10/2014 |
| CN | 203943078 U | 11/2014 |
| CN | 204070570 U | 1/2015 |
| CN | 204146338 U | 2/2015 |
| CN | 102811634 B | 3/2015 |
| CN | 104382237 A | 3/2015 |
| CN | 104470387 A | 3/2015 |
| CN | 104489933 A | 4/2015 |
| CN | 104544559 A | 4/2015 |
| CN | 204317504 U | 5/2015 |
| CN | 104754964 A | 7/2015 |
| CN | 104770878 A | 7/2015 |
| CN | 104799438 A | 7/2015 |
| CN | 104812260 A | 7/2015 |
| CN | 204444239 U | 7/2015 |
| CN | 204763414 U | 11/2015 |
| CN | 105163610 A | 12/2015 |
| CN | 105208882 A | 12/2015 |
| CN | 105208884 A | 12/2015 |
| CN | 105341993 A | 2/2016 |
| CN | 105342011 A | 2/2016 |
| CN | 105357994 A | 2/2016 |
| CN | 205018293 U | 2/2016 |
| CN | 105361250 A | 3/2016 |
| CN | 105453598 A | 3/2016 |
| CN | 205072064 U | 3/2016 |
| CN | 205180371 U | 4/2016 |
| CN | 205197003 U | 5/2016 |
| CN | 205337598 U | 6/2016 |
| CN | 105747281 A | 7/2016 |
| CN | 105789506 A | 7/2016 |
| CN | 105831812 A | 8/2016 |
| CN | 105848503 A | 8/2016 |
| CN | 105876869 A | 8/2016 |
| CN | 205456048 U | 8/2016 |
| CN | 205512358 U | 8/2016 |
| CN | 105939625 A | 9/2016 |
| CN | 205597118 U | 9/2016 |
| CN | 106037014 A | 10/2016 |
| CN | 205648910 U | 10/2016 |
| CN | 106102492 A | 11/2016 |
| CN | 106132217 A | 11/2016 |
| CN | 106163307 A | 11/2016 |
| CN | 205728067 U | 11/2016 |
| CN | 106174699 A | 12/2016 |
| CN | 106231934 A | 12/2016 |
| CN | 205831062 U | 12/2016 |
| CN | 106413439 A | 2/2017 |
| CN | 106413444 A | 2/2017 |
| CN | 106455708 A | 2/2017 |
| CN | 106455714 A | 2/2017 |
| CN | 106455716 A | 2/2017 |
| CN | 106473233 A | 3/2017 |
| CN | 106535680 A | 3/2017 |
| CN | 206097720 U | 4/2017 |
| CN | 106901404 A | 6/2017 |
| CN | 206312988 U | 7/2017 |
| DE | 3302518 A1 | 7/1984 |
| EA | 012169 B1 | 8/2009 |
| EA | 026076 B1 | 2/2017 |
| EP | 1119267 B1 | 7/2004 |
| EP | 2 201 850 A1 | 6/2010 |
| EP | 2253233 A1 | 11/2010 |
| EP | 2022349 B1 | 7/2014 |
| EP | 2 531 053 B1 | 9/2015 |

(56) References Cited

FOREIGN PATENT DOCUMENTS

| | | |
|---|---|---|
| EP | 3098738 A1 | 11/2016 |
| EP | 2 432 339 B1 | 3/2017 |
| EP | 3 179 828 A1 | 6/2017 |
| EP | 3248485 B1 | 4/2020 |
| EP | 3275319 B1 | 8/2020 |
| GB | 2542018 A | 3/2017 |
| GB | 201605104 A | 11/2017 |
| JP | 3-232481 A | 10/1991 |
| JP | 7-184627 A | 7/1995 |
| JP | 11-40122 A | 2/1999 |
| JP | 11-164679 A | 6/1999 |
| JP | 2006-92831 A | 4/2006 |
| JP | 2006-320286 A | 11/2006 |
| JP | 4278306 B2 | 6/2009 |
| JP | 2010526553 A | 8/2010 |
| JP | 2011-87569 A | 5/2011 |
| JP | 3645921 B2 | 5/2011 |
| JP | 2011-518567 A | 6/2011 |
| JP | 4739433 B2 | 8/2011 |
| JP | 2012-527222 A | 11/2012 |
| JP | 2014-500017 A | 1/2014 |
| JP | 2014-79229 A | 5/2014 |
| JP | 2014-521419 A | 8/2014 |
| JP | 2014-525237 A | 9/2014 |
| JP | 2014-533513 A | 12/2014 |
| JP | 2014-534813 A | 12/2014 |
| JP | 2015-503916 A | 2/2015 |
| JP | 2015-504669 A | 2/2015 |
| JP | 2015-508996 A | 3/2015 |
| JP | 2015506170 A | 3/2015 |
| JP | 2015507477 A | 3/2015 |
| JP | 2015524261 A | 8/2015 |
| JP | 2015-180214 A | 10/2015 |
| JP | 2015-529458 A | 10/2015 |
| JP | 2015204833 A | 11/2015 |
| JP | 2016-528910 A | 9/2016 |
| JP | 2016-538848 A | 12/2016 |
| JP | 2017-501682 A | 1/2017 |
| JP | 2017-51189 A | 3/2017 |
| JP | 2017-70297 A | 4/2017 |
| JP | 2017-514463 A | 6/2017 |
| KR | 10-0304044 B1 | 11/2001 |
| KR | 10-0806461 B1 | 2/2008 |
| KR | 20-2009-0008911 U | 9/2009 |
| KR | 100965099 B1 | 4/2010 |
| KR | 101001077 B1 | 12/2010 |
| KR | 10-2011-0096548 A | 8/2011 |
| KR | 101098112 B1 | 12/2011 |
| KR | 2020110009632 U | 12/2011 |
| KR | 10-2012-0027029 A | 3/2012 |
| KR | 10-1184499 B1 | 9/2012 |
| KR | 1020120101637 A | 9/2012 |
| KR | 10-2012-0109634 A | 10/2012 |
| KR | 1020120114333 A | 10/2012 |
| KR | 1020120121314 A | 11/2012 |
| KR | 1020130027909 A | 3/2013 |
| KR | 200466757 Y1 | 4/2013 |
| KR | 10-2013-0081238 A | 7/2013 |
| KR | 20-0469513 Y1 | 10/2013 |
| KR | 1020130139296 A | 12/2013 |
| KR | 1020140068203 A | 6/2014 |
| KR | 1020140092312 A | 7/2014 |
| KR | 10-2014-0116055 A | 10/2014 |
| KR | 10-2014-0118983 A | 10/2014 |
| KR | 10-2014-0119072 A | 10/2014 |
| KR | 1020140135774 A | 11/2014 |
| KR | 10-2015-0030409 A | 3/2015 |
| KR | 10-2015-0033617 A | 4/2015 |
| KR | 10-2015-0058569 A | 5/2015 |
| KR | 10-1516304 B1 | 5/2015 |
| KR | 10-1523088 B1 | 5/2015 |
| KR | 10-1523088 B2 | 5/2015 |
| KR | 10-2015-0099771 A | 9/2015 |
| KR | 10-2016-0009678 A | 1/2016 |
| KR | 10-2016-0012110 A | 2/2016 |
| KR | 10-2016-0015144 A | 2/2016 |
| KR | 1020160012329 A | 2/2016 |
| KR | 10-2016-0040643 A | 4/2016 |
| KR | 10-1609715 B1 | 4/2016 |
| KR | 10-2015-0058569 A | 5/2016 |
| KR | 10-1619032 B1 | 5/2016 |
| KR | 1020160001476 U | 5/2016 |
| KR | 1020160052607 A | 5/2016 |
| KR | 10-2016-0060006 A | 6/2016 |
| KR | 1020160088163 A | 7/2016 |
| KR | 10-2016-0094938 A | 8/2016 |
| KR | 10-2016-0096744 A | 8/2016 |
| KR | 10-2016-0108855 A | 9/2016 |
| KR | 101656061 B1 | 9/2016 |
| KR | 10-2016-0124091 A | 10/2016 |
| KR | 10-1667124 B1 | 10/2016 |
| KR | 10-1668175 B1 | 10/2016 |
| KR | 1020160114743 A | 10/2016 |
| KR | 10-2016-0129024 A | 11/2016 |
| KR | 10-2016-0133665 A | 11/2016 |
| KR | 101679489 B1 | 11/2016 |
| KR | 1020160131035 A | 11/2016 |
| KR | 1020160137627 A | 11/2016 |
| KR | 10-2016-0142896 A | 12/2016 |
| KR | 10-2016-0147253 A | 12/2016 |
| KR | 10-1690389 B1 | 12/2016 |
| KR | 1020160140608 A | 12/2016 |
| KR | 1020170006262 A | 1/2017 |
| KR | 1020170006282 A | 1/2017 |
| KR | 1020170007262 A | 1/2017 |
| KR | 1020170044158 A | 4/2017 |
| KR | 10-2017-0071486 A | 6/2017 |
| KR | 101740160 B1 | 6/2017 |
| KR | 1020170074898 A | 6/2017 |
| RU | 2302806 C2 | 7/2007 |
| RU | 2425608 C2 | 8/2011 |
| RU | 2 531 890 C2 | 10/2014 |
| RU | 2564600 C1 | 10/2015 |
| RU | 2014 125 232 A | 12/2015 |
| RU | 2581999 C2 | 4/2016 |
| RU | 2589437 C2 | 7/2016 |
| RU | 2594557 C2 | 8/2016 |
| RU | 2595593 C2 | 8/2016 |
| RU | 2 602 053 C2 | 11/2016 |
| RU | 2 602 962 C2 | 11/2016 |
| RU | 2603559 C2 | 11/2016 |
| RU | 2 604 012 C2 | 12/2016 |
| RU | 2604012 C2 | 12/2016 |
| UA | 104628 C2 | 2/2014 |
| WO | 9406314 A1 | 3/1994 |
| WO | 98/23171 A1 | 6/1998 |
| WO | 00/27232 A1 | 5/2000 |
| WO | 2010/133342 A1 | 11/2010 |
| WO | 2011/028372 A1 | 3/2011 |
| WO | 2011/095781 A1 | 8/2011 |
| WO | 2012/072264 A1 | 6/2012 |
| WO | 2012/123702 A1 | 9/2012 |
| WO | 2013/034458 A1 | 3/2013 |
| WO | 2013/060743 A2 | 5/2013 |
| WO | 2013/076098 A2 | 5/2013 |
| WO | 2013/098395 A1 | 7/2013 |
| WO | 2013/098398 A3 | 7/2013 |
| WO | 2013/098409 A1 | 7/2013 |
| WO | 2013/102609 A2 | 7/2013 |
| WO | 2013/102612 A2 | 7/2013 |
| WO | 2013/120565 A3 | 8/2013 |
| WO | 2013126777 A2 | 8/2013 |
| WO | 2013/137084 A1 | 9/2013 |
| WO | 2013/171217 A1 | 11/2013 |
| WO | 2014/029880 A2 | 2/2014 |
| WO | 2015/046386 A1 | 4/2015 |
| WO | 2015/088744 A1 | 6/2015 |
| WO | 2015088744 A1 | 6/2015 |
| WO | 2015/128665 A1 | 9/2015 |
| WO | 2015128665 A1 | 9/2015 |
| WO | 2015/155289 A1 | 10/2015 |
| WO | 2015/174657 A1 | 11/2015 |
| WO | 2015165813 A1 | 11/2015 |
| WO | 2015177044 A1 | 11/2015 |

(56) References Cited

FOREIGN PATENT DOCUMENTS

| WO | 2015/197627 A1 | 12/2015 |
|---|---|---|
| WO | 2016/059073 A1 | 4/2016 |
| WO | 2016/075028 A1 | 5/2016 |
| WO | 2016075028 A1 | 5/2016 |
| WO | 2016076147 A1 | 5/2016 |
| WO | 2016107766 A1 | 7/2016 |
| WO | 2016/124550 A1 | 8/2016 |
| WO | 2016124552 A1 | 8/2016 |
| WO | 2016/150019 A1 | 9/2016 |
| WO | 2016/156103 A1 | 10/2016 |
| WO | 2016/156219 A1 | 10/2016 |
| WO | 2016159013 A1 | 10/2016 |
| WO | 2016166064 A1 | 10/2016 |
| WO | 2016178377 A1 | 11/2016 |
| WO | 2016/187803 A1 | 12/2016 |
| WO | 2017/029088 A1 | 2/2017 |
| WO | 2017/029089 A1 | 2/2017 |
| WO | 2017/037457 A1 | 3/2017 |
| WO | 2017/075759 A1 | 5/2017 |
| WO | 2017042297 A1 | 6/2017 |
| WO | 2017/139963 A1 | 8/2017 |
| WO | 2018050449 A1 | 3/2018 |
| WO | 2018/182322 A1 | 10/2018 |
| WO | 2018/189195 A1 | 10/2018 |
| WO | 2019020826 A1 | 1/2019 |
| WO | 2019/030172 A1 | 2/2019 |
| WO | 2019095268 A1 | 5/2019 |

OTHER PUBLICATIONS

Office Action dated Sep. 29, 2021 in Chinese Application No. 201880024311.8.
Office Action dated Sep. 24, 2021 in Chinese Application No. 201880024010.5.
Office Action dated Sep. 29, 2021 in Chinese Application No. 201880024276.X.
Office Action dated Oct. 28, 2021 in Chinese Application No. 201880046418.2.
Extended European Search Report dated Oct. 27, 2021 in European Application No. 18844735.3.
Office Action dated Sep. 17, 2021 in Chinese Application No. 201880030699.2.
Partial supplementary European search report dated Aug. 3, 2020 in Application No. 17880867.1.
Extended European search report dated Nov. 4, 2020 by the European Patent Office in Application No. 17880867.1.
Office Action dated Oct. 29, 2020 by the Korean Patent Office in Application No. 10-2018-0010837.
Office Action dated Nov. 4, 2020 by the Japanese Patent Office in Application No. 2019-554453.
Office Action dated Nov. 4, 2020 by the Japanese Patent Office in Application No. 2020-128346.
Decision on Grant dated Nov. 26, 2020 by the Russian Federal Service For Intellectual Property Patent Application No. 2020124607.
Office Action dated Nov. 26, 2020 by Russian Federal Service For Intellectual Property Office Patent Application No. 2020124609.
Decision on Grant dated Oct. 26, 2020 by Russian Federal Service For Intellectual Property in Application No. 2020124610.
Office Action dated Jun. 29, 2020 by the Korean Patent Office in Application No. 10-2018-0010836.
Communication dated Jan. 27, 2022 from the Vietnamese Patent Office in Vietnamese Application No. 1-2019-06063.
Communication dated Nov. 25, 2021 from the Chinese Patent Office in Chinese Application No. 201880047174.X.
Communication dated Dec. 1, 2021 from the Chinese Patent Office in Chinese Application No. 201880046367.3.
Notice of Non-Final Rejection dated Feb. 13, 2020, from the Korean Intellectual Property Office in Application No. 10-2018-0010837.
Office Action dated Jan. 8, 2020 in Korean Application No. 10-2017-0119664.
Office Action dated Dec. 11, 2019 in Korean Application No. 10-2018-0010841.
Office Action dated Jan. 3, 2020 in Korean Application No. 10-2018-0012456.
Office Action dated Jan. 3, 2020 in Korean Application No. 10-2018-0018693.
Office Action dated Jul. 3, 2019 in Korean Application No. 10-2019-0017391.
International Search Report dated May 29, 2018 in International Application No. PCT/KR2017/012486.
International Search Report dated Sep. 6, 2018 in International Application No. PCT/KR2018/004179.
International Search Report dated Nov. 26, 2018 in International Application No. PCT/KR2018/009094.
International Search Report dated Feb. 28, 2019 in International Application No. PCT/KR2018/009100.
Extended European Search Report dated Jan. 14, 2021 in European Application No. 18783776.0.
Extended European Search Report dated Jan. 25, 2021 in European Application No. 18785166.2.
Extended European Search Report dated Jan. 29, 2021 in European Application No. 18784464.2.
Extended European Search Report dated Mar. 15, 2021 in European Application No. 18785061.5.
Extended European Search Report dated Mar. 19, 2021 in European Application No. 18784164.8.
Extended European Search Report dated Mar. 24, 2021 in European Application No. 18784268.7.
Extended European Search Report dated Mar. 25, 2021 in European Application No. 18784370.1.
Extended European Search Report dated Mar. 25, 2021 in European Application No. 18784841.1.
Office Action dated Feb. 24, 2021 in Japanese Application No. 2019-555168.
Office Action dated Feb. 24, 2021 in Japanese Application No. 2019-555203.
Office Action dated Feb. 24, 2021 in Japanese Application No. 2019-555204.
Office Action dated Feb. 4, 2021 in Russian Application No. 2020124609.
Office Action dated Feb. 9, 2021 in Japanese Application No. 2019-555184.
Office Action dated Jan. 26, 2021 in Japanese Application No. 2020-501521.
Office Action dated Mar. 2, 2021 in Japanese Application No. 2019-555170.
Office Action dated Mar. 2, 2021 in Japanese Application No. 2019-555182.
Office Action dated Mar. 30, 2021 in Japanese Application No. 2020-501377.
Office Action dated Jan. 19, 2021 in Indonesian Application No. P00201906007.
Communication dated Apr. 2, 2019, from the Korean Intellectual Property in application No. 10-2019-0021286.
Communication dated Apr. 3, 2019, from the Korean Intellectual Property in application No. 10-20190018812.
Communication dated Apr. 4, 2019, from the Korean Intellectual Property in application No. 10-1020190020484.
Communication dated Apr. 4, 2019, from the Korean Intellectual Property in application No. 1020190019194.
Communication dated Apr. 4, 2019, , from the Korean Intellectual Property in application No. 1020190019195.
Communication dated Apr. 5, 2019, , from the Korean Intellectual Property in application No. 1020190027638.
Communication dated Apr. 25, 2019, , from the Korean Intellectual Property in application No. 1020190033721.
Communication dated Apr. 25, 2019, , from the Korean Intellectual Property in application No. 1020190033784.
Communication dated Apr. 9, 2021, from the Korean Intellectual Property in application No. 102020116256.
Communication dated Jul. 22, 2021, from the Korean Intellectual Property in application No. 1020210051359.

(56) References Cited

OTHER PUBLICATIONS

Communication dated May 5, 2021, from the Canadian Intellectual Property in application No. 3047236.
Communication dated Jan. 15, 2021 ,European Patent Office in application No. 20188949.0.
Communication dated Apr. 1, 2021, from the European patent Office in application No. 18805933.1.
Communication dated Jul. 1, 2021, from the European Patent Office in application No. 18854661.8.
Communication dated Jun. 14, 2021, from the European Patent Office in application No. 18842951.8.
Communication dated Jul. 27, 2021 by the Chinese Patent Office in Chinese Application No. 201780084891.5.
Communication dated Jun. 29, 2021 by the Chinese Patent Office in Chinese Application No. 201880022072.2.
Communication dated Aug. 16, 2021 by the Chinese Patent Office in Chinese Application No. 201880024006.9.
Communication dated Aug. 26, 2021 by the Chinese Patent Office in Chinese Application No. 201880024107.6.
Communication dated Aug. 4, 2021 by the Chinese Patent Office in Chinese Application No. 201880024289.7.
Communication dated Jul. 26, 2021 by the Chinese Patent Office in Chinese Application No. 201880024059.0.
Communication dated Jul. 16, 2021 by the Chinese Patent Office in Chinese Application No. 201880024367.3.
Communication dated Jul. 19, 2021 by the Chinese Patent Office in Chinese Application No. 201880024070.7.
Office Action dated May 27, 2020 in Russian Application No. 2019121813.
Extended European Search Report dated Jun. 16, 2021 in European Application No. 18853434.1.
International Search Report dated Jul. 24, 2018, In International Application No. PCT/KR2018/003691.
International Search Report dated Sep. 6, 2018 , In International Application No. PCT/KR2018/004176.
International Search Report dated Nov. 14, 2018, In International Application No. PCT/KR2018/004118.
International Search Report dated Nov. 6, 2018, In International Application No. PCT/KR2018/004178.
International Search Report dated Sep. 7, 2018, In International Application No. PCT/KR2018/004171.
International Search Report dated Sep. 7, 2018, In International Application No. PCT/KR2018/004172.
International Search Report dated Nov. 6, 2018, In International Application No. PCT/KR2018/004129.
International Search Report dated Nov. 6, 2018, In International Application No. PCT/KR2018/004130.
International Search Report dated Aug. 29, 2018, In International Application No. PCT/KR2018/005945.
International Search Report dated Nov. 30, 2018, In International Application No. PCT/KR2018/006702.
International Search Report dated Dec. 4, 2018, In International Application No. PCT/KR2018/006747.
Extended European Search Report dated Dec. 11, 2020 in European Application No. 20188967.2.
Extended European Search Report dated Jan. 15, 2021 in European Application No. 20188949.0.
Extended European Search Report dated Dec. 16, 2020 in European Application No. 20188985.4.
Office Action dated Dec. 30, 2020 in Russian Application No. 2020124651.
Office Action dated Dec. 28, 2020 in Russian Application No. 2020124652.
Office Action dated Dec. 11, 2020 in Russian Application No. 2020124653.
Office Action dated Jan. 22, 2021 in Russian Application No. 2020124657.
Office Action dated Jan. 22, 2021 in Russian Application No. 2020124658.
Extended European Search Report dated Dec. 18, 2020 in European Application No. 18775504.6.
Office Action dated Jan. 19, 2021 in Japanese Application No. 2019-553569.
Extended European Search Report dated Jan. 14, 2021 in European Application No. 18784738.9.
Extended European Search Report dated Dec. 10, 2020 in European Application No. 20188932.6.
Office Action dated Jan. 12, 2021 in Japanese Application No. 2019-555201.
Office Action dated Jan. 12, 2021 in Japanese Application No. 2019-555169.
Office Action dated Jan. 5, 2021 in Japanese Application No. 2019-558557.
Extended European Search Report dated Nov. 19, 2020 in European Application No. 20188792.4.
Office Action dated Dec. 1, 2020 in Japanese Application No. 2020-501188.
Extended European Search Report dated Dec. 18, 2020 in European Application No. 20188926.8.
Office Action dated Jan. 19, 2021 in Japanese Application No. 2020-501514.
Office Action dated May 28, 2020 in Korean Application No. 10-2017-0147605.
Communication dated Mar. 14, 2022 from the Chinese Patent Office in Chinese Application No. 201880024059.0.
Communication dated Feb. 28, 2022 from the Chinese Patent Office in Chinese Application No. 201880050526.7.
Office Action dated Jun. 28, 2022, issued in Japanese Application No. 2021-075028.
Office Action dated May 29, 2022, issued in Philippines Application No. 1/2019/501361.
Office Action dated May 30, 2022, issued in Canadian Application No. 3,080,145.
Office Action dated Aug. 12, 2022, issued in Chinese Application No. 201880024059.0.
Office Action dated Sep. 20, 2022 from the Japanese Patent Office in JP Application No. 2021-174035.
Office Action dated Oct. 24, 2022 from the Ukrainian Patent Office in UA Application No. a202004868.
Office Action dated Oct. 27, 2022 from the Ukrainian Patent Office in UA Application No. a202004869.
Office Action dated Nov. 2, 2022 from the China National Intellectual Property Administration in CN Application No. 201880050526.7.
Office Action dated Nov. 22, 2022 from the China National Intellectual Property Administration in CN Application No. 202010762996.5.
Office Action dated Jan. 10, 2023, issued in Chinese Application No. 202010760990.4.
Office Action dated Jan. 3, 2023, issued in Chinese Application No. 202010760979.8.
Office Action dated Jan. 28, 2023, issued in Chinese Application No. 202010763214.X.
Office Action dated Jan. 10, 2023, issued in Japanese Application No. 2021-177649.
Office Action dated Dec. 30, 2022, issued in Chinese Application No. 202010756239.7.
Office Action dated Dec. 13, 2022, issued in Japanese Application No. 2021-165298.

\* cited by examiner

AEROSOL GENERATION DEVICE AND CONTROL METHOD FOR AEROSOL GENERATION DEVICE

TECHNICAL FIELD

One or more exemplary embodiments relate to an aerosol generation device and a control method for the aerosol generation device, and more particularly, to an aerosol generation device including a power supply source that is capable of being recharged quickly and provides high output, and a control method for the aerosol generation device.

BACKGROUND ART

Aerosol generation devices according to the related art, which are operated electrically, have a similar size to that of cigarettes, and include a heater and a battery to heat an aerosol-forming substrate of an aerosol-generating product. The battery may provide a high output, for a cycle of several minutes, to a heater in the aerosol generation device. The battery included in the aerosol generation device may be a battery that is capable of being recharged hundreds to thousands times for a new smoking session.

The aerosol generation device may be operated by sensing inhalation by a user. Upon sensing the inhalation by the user, the heater included in the aerosol generation device may be heated to a temperature sufficient to generate aerosol from an aerosol-forming substrate of an aerosol-generating product. After the heater is heated to the temperature sufficient to generate aerosol, the aerosol generation device may maintain the temperature of the heater until the user continues smoking.

When smoking, users of an aerosol generation device may wish for the heater of the aerosol generation device to heat up quickly. In addition, after one smoking session, users may wish to quickly charge the aerosol generation device for a new smoking session.

DESCRIPTION OF EXEMPLARY EMBODIMENTS

Technical Problem

Provided is a power supply source that enables quick heating of a heater of an aerosol generation device and high-speed charging of the aerosol generation device.

By including a plurality of power sources in an aerosol generation device, the plurality of power sources are selectively operated according to whether a high output is required in the aerosol generation device or not.

Solution to Problem

According to an aspect of the present disclosure, by using a plurality of power sources, a method of selectively operating the plurality of power sources according to whether a high output is required in the aerosol generation device or not, is provided.

Advantageous Effects of Disclosure

According to the exemplary embodiments, a power supply source that enables quick heating of a heater of an aerosol generation device and high-speed charging of the aerosol generation device may be provided.

According to the exemplary embodiments, by including a plurality of power sources in an aerosol generation device, the plurality of power sources may be selectively operated according to whether a high output is required in the aerosol generation device or not.

BEST MODE

Figure 1:
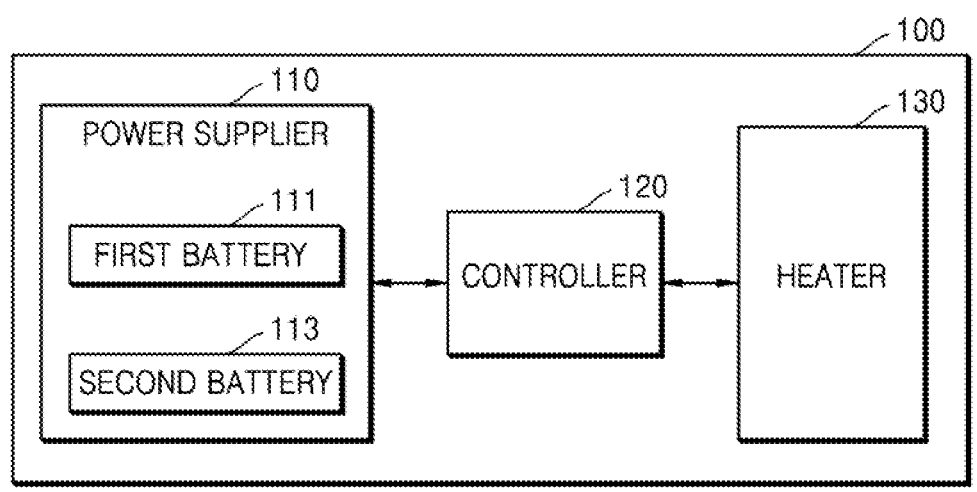
FIG. 1 is a block diagram of an aerosol generation device 100 according to an exemplary embodiment.

An aerosol generation device according to an exemplary embodiment includes: a power supplier including a first battery and a second battery; a controller; and a heater, wherein the controller is configured to control the power supplier to operate according to one of a first mode in which the first battery supplies power to the heater and a second mode in which the second battery supplies power to the heater, and control the power supplier to supply greater power in the first mode than in the second mode.

The first mode may be a mode for raising a temperature of the heater, and the second mode may be a mode for maintaining the temperature of the heater.

The first battery may include a lithium-ion capacitor.

The second battery may include one of a lithium-ion cell battery, a lithium iron phosphate battery, a lithium-titanate battery, and a lithium polymer battery.

The aerosol generation device may further include a sensor for sensing inhalation by a user, wherein, upon sensing the inhalation, the controller may control the power supplier to operate according to the first mode.

The aerosol generation device may further include a sensor for sensing inhalation by a user; and a sensor for measuring a temperature of the heater, wherein, upon sensing the inhalation, the controller controls the power supplier to operate according to the first mode when the temperature of the heater is equal to or lower than a first temperature and controls the power supplier to operate according to the second mode when the temperature of the heater is higher than the first temperature.

The controller may be configured to control the power supplier to operate according to the first mode while the temperature of the heater is raised to a threshold temperature, and when the temperature of the heater reaches the threshold temperature or higher, the controller may control the power supplier to operate according to the second mode.

The controller may be configured to control the power supplier to operate according to the first mode for a first period, and when the first period ends, the controller may control the power supplier to operate according to the second mode.

The aerosol generation device may further include a memory storing a condition, under which the first mode is switched to the second mode.

The condition may include a temperature of the heater and a period of time during which the power supplier is operated according to the first mode.

A control method of controlling an aerosol generation device, according to an exemplary embodiment, includes:

when inhalation by a user is sensed and a temperature of a heater is equal to or lower than a first temperature, controlling a power supplier to operate according to a first mode in which a power supplier supplies power to a heater by using a first battery; and controlling the power supplier to operate according to one of the first mode and a second mode, based on the temperature of the heater or a period of time during which the power supplier is operated according to the first mode, wherein the power supplier supplies greater power to the heater in the first mode than in the second mode, wherein power is supplied to the heater by using a second battery.

The first mode may be a mode for raising the temperature of the heater, and the second mode may be a mode for maintaining the temperature of the heater.

The first battery may include a lithium-ion capacitor.

The second battery may include one of a lithium-ion cell battery, a lithium iron phosphate battery, a lithium-titanate battery, and a lithium polymer battery.

The method may further include controlling the power supplier to operate according to the second mode when the inhalation is sensed and the temperature of the heater exceeds the first temperature.

The method may further include: controlling the power supplier to operate according to the first mode while the temperature of the heater is raised to a threshold temperature; and controlling the power supplier to operate according to the second mode when the temperature of the heater is equal to or higher than the threshold temperature.

The method may further include: controlling the power supplier to operate according to the first mode for a first period; and controlling the power supplier to operate according to the second mode when the first period ends.

MODE OF DISCLOSURE

Hereinafter, exemplary embodiments according to the present disclosure will be described in detail with reference to the attached drawings. In addition, a method of configuring and using an electronic device according to exemplary embodiments of the present disclosure will be described in detail with reference to the attached drawings. Like reference numerals or marks in the drawings denote parts or components performing substantially the same function.

Terms including ordinal numbers such as 'first,' 'second,' etc. are used to describe various components but the components should not be defined by these terms. Such terms are used only for the purpose of distinguishing one constituent component from another constituent component. For example, a first component discussed below could be termed a second component, and similarly, a second component may be termed a first component, without departing from the teachings of this disclosure. The term "and/or" includes any one of a plurality of related items or a combination of a plurality of related items.

The terms used in the present specification are merely used to describe exemplary embodiments, and are not intended to limit the present disclosure. The singular forms "a," "an" and "the" are intended to include the plural forms as well, unless the context clearly indicates otherwise. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, exemplary embodiments of the present disclosure will be described in detail with reference to the drawings.

FIG. 1 is a block diagram of an aerosol generation device 100 according to an exemplary embodiment.

The aerosol generation device 100 illustrated in FIG. 1 may include a plurality of power sources and selectively operate the plurality of power sources.

The aerosol generation device 100 may include a power supplier 110, a controller 120, and a heater 130.

The power supplier 110 according to an exemplary embodiment may include a plurality of power sources. For example, the power supplier 110 may include a first battery 111 and a second battery 113.

The first battery 111 may be a power source used to supply power to the heater 130 according to a first mode. For example, the first mode may be a mode to increase a temperature of the heater 130 to a temperature to generate aerosol (preheating mode).

The first battery 111 according to an exemplary embodiment may include a lithium-ion capacitor. The first battery 111 may include, for example, two or more lithium-ion capacitor groups. Each group may include one or more lithium-ion capacitors that are serially connected.

When the first battery 111 is a lithium-ion capacitor according to an exemplary embodiment, an average rate of charging and discharging of the first battery 111 may be about 50 C (C-rate), but is not limited thereto. For example, when the first battery 111 is a lithium-ion capacitor, the first battery 111 may be charged or discharged about five to ten times faster than a lithium iron phosphate battery.

In addition, when the first battery 111 is a lithium-ion capacitor according to an exemplary embodiment, the available number of times of charging or discharging of the battery may be increased by about two to four times compared with a lithium iron phosphate battery. For example, the available number of times of use of the lithium iron phosphate battery by repeating full charging and discharging of the battery is about 2000 times, whereas in the case when the first battery 111 is a lithium-ion capacitor, the available number of times of full charging and discharging of the first battery 111 may be about 8000 times.

Here, whether a battery is fully charged or fully discharged may be determined based on a level of power stored in the battery compared to the total battery capacity. For example, when power stored in the battery is equal to or greater than 95% of the total capacity, it may be determined that the battery is fully charged. Furthermore, when power stored in the battery is 10% or less of the total capacity, it may be determined that the battery is completely discharged. However, the criteria for determining whether a battery is fully charged or completely discharged are not limited to the above examples.

The second battery 113 may be a power source used to supply power to the heater 130 according to a second mode. For example, the second mode may be a mode to maintain a temperature of the heater 130 (smoking mode).

The second battery 113 according to an exemplary embodiment may include one of a lithium-ion cell battery, a lithium iron phosphate battery, a lithium-titanate battery, and a lithium polymer battery.

According to an exemplary embodiment, greater power may be supplied to the heater 130 in the first mode than in the second mode.

The first mode may be a mode in which high output is required for a short period of time, and the second mode may be a mode that does not require such high output.

For example, the first mode may include a preheating mode. The preheating mode is a mode in which the heater 130 is heated to a temperature to generate aerosol when a user is about to start smoking. In the preheating mode, the temperature of the heater 130 is to be heated at room temperature to about 200 degrees, and thus high output is necessary.

The second mode may include a smoking mode. The smoking mode is a mode in which the temperature of the heater 130 is maintained when a user continues smoking after the heater 130 is preheated to a temperature appropriate to generate aerosol. To maintain the temperature of the heater 130 in the smoking mode, no high output is required, compared with when preheating the heater 130.

When the first battery is a lithium-ion capacitor according to an exemplary embodiment, about ten seconds may be required to raise the temperature of the heater 130 in the preheating mode to a temperature to generate aerosol.

According to an exemplary embodiment, when supplying power to the heater 130 according to the preheating mode, and a lithium-ion capacitor is used as the first battery, the time required for preheating of the heater 130 may be reduced to ⅓, compared with when using a lithium iron phosphate battery.

The controller 120 is configured to control the operation of the aerosol generation device 100. Specifically, the controller 120 controls operations of not only the battery 3110 and the heater 130 but also other components included in the aerosol generation device 100. Also, the controller 120 may identify the state of each component of the aerosol generation device 100 to determine whether the aerosol generation device 100 is in an operable state.

The controller 120 may include a microprocessor or a micro-controller. For example, the controller 120 may be implemented as an array of a plurality of logic gates or can be implemented as a combination of a general purpose microprocessor and a memory in which a program executable in the microprocessor is stored. It will be understood by one of ordinary skill in the art that the processor can be implemented in other forms of hardware.

Upon sensing user's inhalation, the controller 120 may control a power supplier to operate according to the preheating mode. A user's inhalation may be sensed using an additional sensor (not shown).

The aerosol generation device 100 according to an exemplary embodiment may also enter the preheating mode as the user turns on an additional switch (not shown).

While a temperature of the heater 130 is increased to a threshold temperature, the controller 120 may control the power supplier 110 to operate according to the first mode, and when the temperature of the heater 130 is equal to or higher than the threshold temperature, the controller 120 may control the power supplier 110 to operate according to the second mode.

The threshold temperature may be a temperature appropriate for aerosol to be generated from an aerosol-forming substrate. The threshold temperature may be differently set according to a type of an aerosol-forming substrate that is to be heated using the heater 130.

The controller 120 may control the power supplier to operate according to the first mode for a first period, and when the first period passes, the controller 120 may control the power supplier to operate according to the second mode.

The first period according to an exemplary embodiment may be a period of time required for a temperature of the heater 130 to be raised to a threshold temperature suitable for generating aerosol from an aerosol-forming substrate.

Meanwhile, the controller 120 may sense a user's inhalation, and when the temperature of the heater 130 is equal to or lower than a first temperature, the controller 120 may control the power supplier 110 to operate according to the first mode. The first temperature may be set to, for example, about 60% to 80% of a threshold temperature appropriate for aerosol to be generated from an aerosol-forming substrate.

The first temperature may be in the range of 300 degrees to 350 degrees, and the range may be appropriately modified according to a type of cigarette.

When the temperature of the heater 130 is equal to or lower than the first temperature, after sensing user's inhalation, a relatively high output may be required to raise the temperature of the heater 130 to the threshold temperature. In this case, the controller 120 may control the power supplier 110 to operate according to the first mode in which the first battery 111 is used.

In addition, the controller 3120 may sense a user's inhalation, and when the temperature of the heater 130 exceeds the first temperature, the controller 120 may control the power supplier 110 to operate according to the second mode.

When the temperature of the heater 130 exceeds the first temperature, after sensing user's inhalation, a relatively high output may not be required to raise the temperature of the heater 130 to the threshold temperature. In this case, the controller 120 may control the power supplier 110 to operate according to the second mode in which the second battery 113 is used.

The first temperature may be differently set according to a type of an aerosol-forming substrate to be heated using the heater 130. In addition, the first temperature may be differently set according to the aerosol generation device 100.

Also, the controller 120 may check the presence or absence of a user's puff, check the strength of the puff, and count the number of puffs. Furthermore, the controller 120 may continuously check the duration of the operation of the aerosol generation device 100. In addition, the controller 120 may check whether a charging device, which will be described later, is coupled to the aerosol generation device 100, and control operation of the aerosol generation device 100 according to whether the charging device and the aerosol generation device 100 are coupled to or separated from each other.

The heater 130 may be configured to heat an aerosol-forming substrate by using power supplied from the power supplier 110.

When the aerosol-forming substrate is accommodated in a cavity, the heater 3130 may be located inside the aerosol-forming substrate. Therefore, the heated heater 3130 may raise the temperature of an aerosol generating material included in the aerosol-forming substrate.

The heater 130 may be an electrical resistive heater. For example, the heater 130 may include an electrically conductive track, and the heater 130 may be heated as current flows through the electrically conductive track.

The heater 130 may include at least one electrically conductive track (a first electrically conductive track and a second electrically conductive track). For example, the heater 130 may include, but is not limited to, a first electrically conductive track including two electrically conductive track and a second electrically conductive track including one or two electrically conductive tracks. For example, the heater 130 may further include a second electrically conductive track for sensing temperature in addition to a first electrically conductive track for heating.

For example, when a voltage applied to the second electrically conductive track and a current flowing through the second electrically conductive track are measured, a resistance R may be determined, and a temperature T of the second electrically conductive track may be determined according to the resistance.

An electrically conductive track includes an electro-resistive material. For example, the electrically conductive track may include a metal. In another example, an electrically conductive track may include an electrically conductive ceramic material, carbon, a metal alloy, or a composite of a ceramic material and a metal.

For stable use, the heater 130 may be supplied with power according to the specifications of 3.2 V, 2.4 A, and 8 W, but is not limited thereto. For example, when power is supplied to the heater 130, the surface temperature of the heater 130 may rise to 400° C. or higher. The surface temperature of the heater 130 may rise to about 350° C. before 15 seconds after the power supply to the heater 130 starts.

Figure 2:
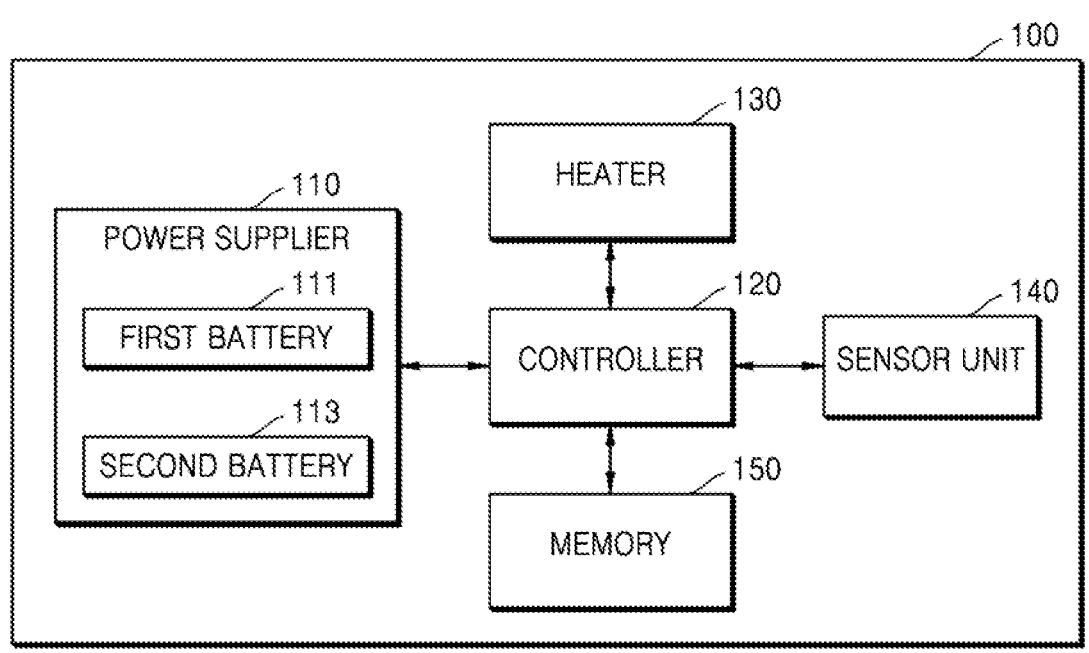
FIG. 2 is another block diagram of an aerosol generation device 100 according to an exemplary embodiment.

FIG. 2 is another block diagram of an aerosol generation device 100 according to an exemplary embodiment.

According to an exemplary embodiment, the aerosol generation device 100 may include the power supplier 110, the controller 120, the heater 130, a sensor unit 140, and a memory 150.

Description of the power supplier 110, the controller 120, and the heater 130 provided with reference to FIG. 1 will be omitted here.

The sensor unit 140 according to an exemplary embodiment may include a sensor for detecting a temperature of a heater.

In addition, the sensor unit 140 may not be configured as an additional temperature sensor, but may be included in the heater 130 to function as a temperature sensor.

Also, the aerosol generation device 100 may include both an electrically conductive track functioning as a temperature detecting sensor and a temperature detecting sensor.

In addition, the sensor unit 140 may include an inhalation sensor for detecting a user's inhalation. An inhalation sensor includes a sensor capable of detecting an air flow or a change in air pressure due to a user's inhalation.

The memory 150 according to an exemplary embodiment may store various data, programs or applications to drive and control the aerosol generation device 100.

In addition, the memory 150 may store a condition under which the first mode is switched to the second mode. The condition, under which the first mode is switched to the second mode, may include a heater temperature and a period of time during which the power supplier is operated according to the first mode.

While the memory 150 is illustrated as an additional component apart from the controller 120, the memory 150 may also be a component included in the controller 120.

The aerosol generation device 100 may further include general-purpose components in addition to the power supplier 110, the controller 120, the heater 130, the sensor unit 140, and the memory 150.

For example, the aerosol generation device 100 may include a display capable of outputting visual information or a motor for outputting tactile information. As an example, when the display is included in the aerosol generation device 100, the controller 120 may transmit, to a user via the display, information related to a state of the aerosol generation device 100 (e.g., whether the aerosol generation device 100 is available), information related to the heater 130 (e.g., a preheating start, a preheating progress, a preheating completion, etc.), information related to the power supplier 110 (e.g., remaining capacity of the battery of the power supplier 110, whether the power supplier 110 is available, etc.), information related to a reset of the aerosol generation device 100 (e.g., a reset time, a reset progress, a reset completion, etc.), information related to cleaning of the aerosol generation device 100 (e.g., a cleaning time, necessity of cleaning, a cleaning progress, a cleaning completion, etc.), information related to charging of the aerosol generation device 100 (e.g., necessity of charging, a charging progress, a charging completion, etc.), information related to a puff (e.g., the number of puffs, notification of expected completion of puffs, the strength of puffs, etc.), or information related to safety (e.g., lapse of time of use, etc.). As another example, when the motor is included in the aerosol generation device 100, the controller 120 may generate a vibration signal by using the motor, thereby transmitting the above-described information to the user.

In addition, the aerosol generation device 100 may include a terminal coupled with at least one input device (e.g., a button), through which a user may control the function of the aerosol generation device 100, and/or with the charging device. For example, the user may perform various functions by using the input device of the aerosol generation device 100. By adjusting the number of times (e.g., once or twice) that the user presses the input device or a time (e.g., 0.1 second, 0.2 second, etc.) during which the user is pressing the input device, the user may perform a desired function among a plurality of functions of the aerosol generation device 100. As a user manipulates the input device, the aerosol generation device 100 may perform a function of preheating the heater 130, a function of regulating the temperature of the heater 130, a function of cleaning the space in which a cigarette is inserted, a function of checking whether the aerosol generation device 100 is in an operable state, a function of displaying the remaining power (available power) of the battery 3110, a function of resetting the aerosol generation device 100, etc. However, the function of the aerosol generation device 100 is not limited to the examples described above.

In addition, the aerosol generation device 100 may include a puff detecting sensor, a temperature detecting sensor, and/or a cigarette insertion detecting sensor. For example, the puff detecting sensor may be implemented by a common pressure sensor, and the cigarette insertion detecting sensor may be implemented by a common capacitive sensor or a resistance sensor. In addition, the aerosol generation device 100 may be manufactured in a structure in which an external air may be introduced/discharged even when the cigarette is inserted.

Figure 3:
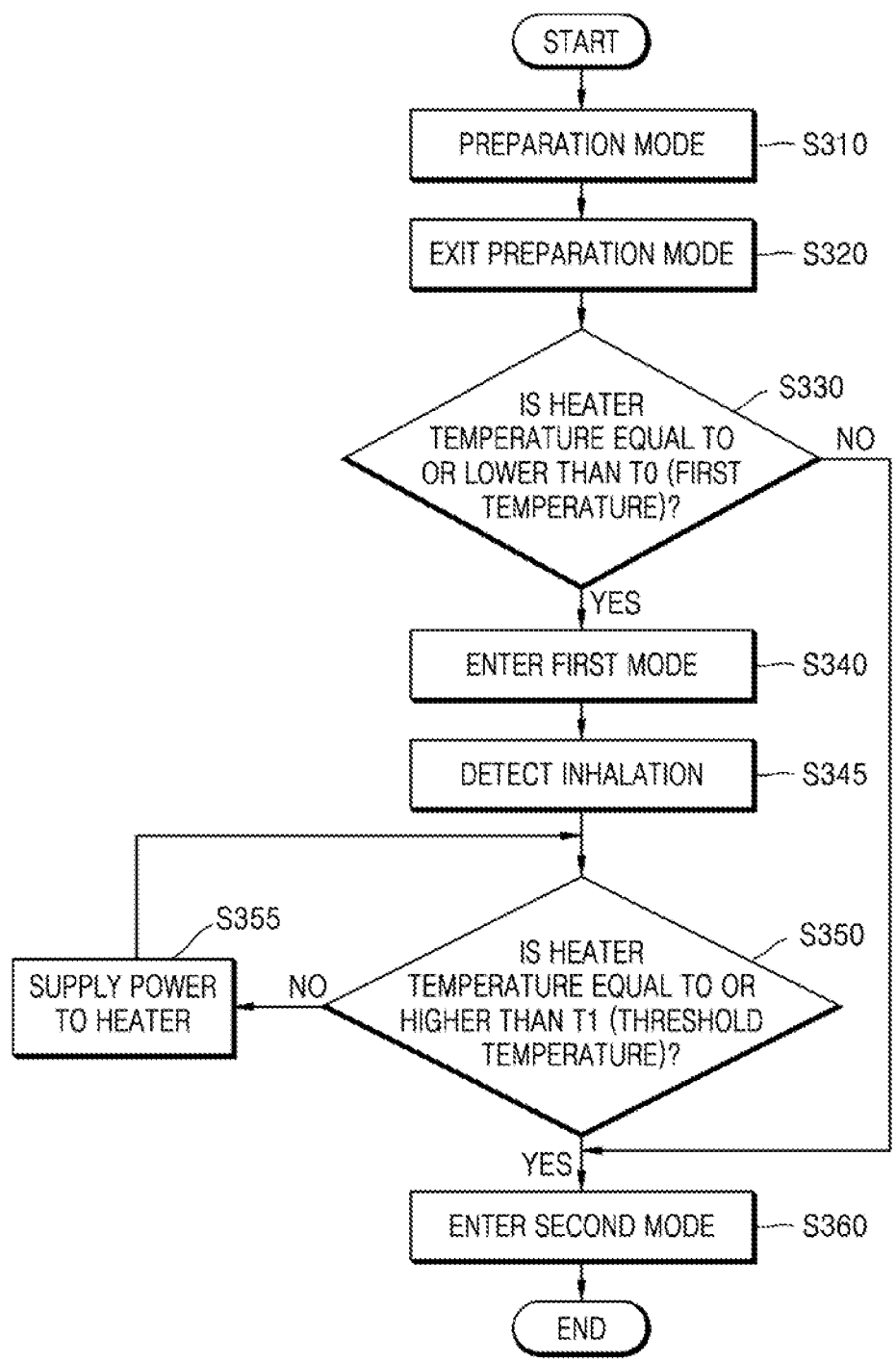
FIG. 3 is a flowchart of a control method for an aerosol generation device according to an exemplary embodiment.

FIG. 3 is a flowchart of a control method for an aerosol generation device according to an exemplary embodiment.

In detail, FIG. 3 illustrates that the aerosol generation device 100 according to an exemplary embodiment is switched from the first mode to the second mode according to whether a heater temperature is equal to or higher than T1 (threshold temperature).

In operation S310, the aerosol generation device 100 may be in a preparation mode (S310).

A preparation mode according to an exemplary embodiment may be a mode in which the aerosol generation device 100 is controlled to consume minimum power. The preparation mode may also be referred to as a low-power mode.

In operation S320, the aerosol generation device 100 may exit the preparation mode (S320). The preparation mode may be exited when there is a need to preheat the aerosol generation device 100. For example, when a user's pressing a button included in the aerosol generation device 100 is sensed, or when insertion of a cigarette into the aerosol generation device 100 is sensed, or when it is determined that the aerosol generation device 100 needs to be cleaned, the aerosol generation device 100 may exit the preparation mode.

In operation S330, the aerosol generation device 100 may determine whether a heater temperature is equal to or lower than T0 (first temperature) (S330). The first temperature according to an exemplary embodiment may be set to, for example, about 60% to about 80% of a threshold temperature T1 that is a temperature required for aerosol to be generated from an aerosol-forming substrate.

The first temperature may be in the range of 300 degrees to 350 degrees, and the range may be appropriately modified according to a type of cigarette.

When the heater temperature is determined to be equal to or lower than T0 (first temperature) in operation S330, in operation S340, the aerosol generation device 100 may enter the first mode (S340). When the heater temperature is determined to be above T0 (first temperature) in operation S330, the aerosol generation device 100 may enter the second mode (S360).

In operation S345, the aerosol generation device 100 may detect a user's inhalation (S345).

In operation S350, the aerosol generation device 100 may determine whether the heater temperature is equal to or higher than T1 (threshold temperature) (S350).

When the heater temperature is determined to be equal to or higher than T1 (threshold temperature) in operation S350, in operation S360, the aerosol generation device 100 may enter the second mode (S360). When the heater temperature is determined to be not equal to or higher than T1 (threshold temperature) in operation S350, the aerosol generation device 100 may supply power to the heater (S355). In operation S355, the aerosol generation device 100 may be maintained in the first mode and additionally supply power to the heater.

Figure 4:
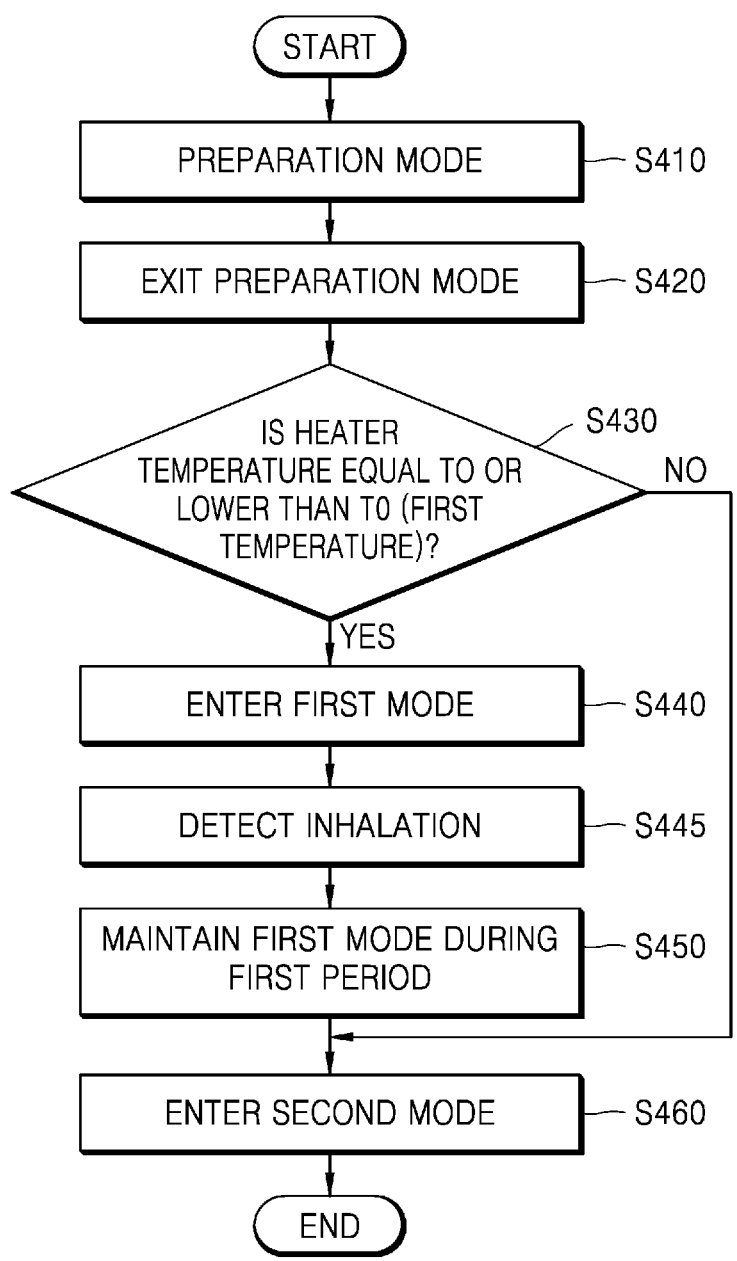
FIG. 4 is another flowchart of a control method for an aerosol generation device according to an exemplary embodiment.

FIG. 4 is another flowchart of a control method for an aerosol generation device according to an exemplary embodiment.

In detail, FIG. 4 illustrates that the aerosol generation device 100 according to an exemplary embodiment is switched from the first mode to the second mode according to whether a first period has passed after the aerosol generation device 100 has entered the first mode.

Description of the flowchart of FIG. 4 provided with reference to the flowchart of FIG. 3 will be omitted here.

In operation S410, the aerosol generation device 100 may be in a preparation mode (S410).

In operation S420, the aerosol generation device 100 may exit the preparation mode (S420).

In operation S430, the aerosol generation device 100 may determine whether a heater temperature is equal to or lower than T0 (first temperature) (S430).

When the heater temperature is determined to be equal to or lower than T0 (first temperature) in operation S430, in operation S440, the aerosol generation device 100 may enter the first mode (S440). When the heater temperature is determined to be above T0 (first temperature) in operation S430, the aerosol generation device 100 may enter the second mode (S460).

In operation S445, the aerosol generation device 100 may detect a user's inhalation (S445).

In operation S450, the aerosol generation device 100 may be maintained in the first mode for a first period. The first period may be a period of time required for a temperature of the heater to be raised to a threshold temperature suitable for generating aerosol from an aerosol-forming substrate.

In operation S460, after the first period has passed, the aerosol generation device 100 may enter the second mode (S460).

Figure 5:
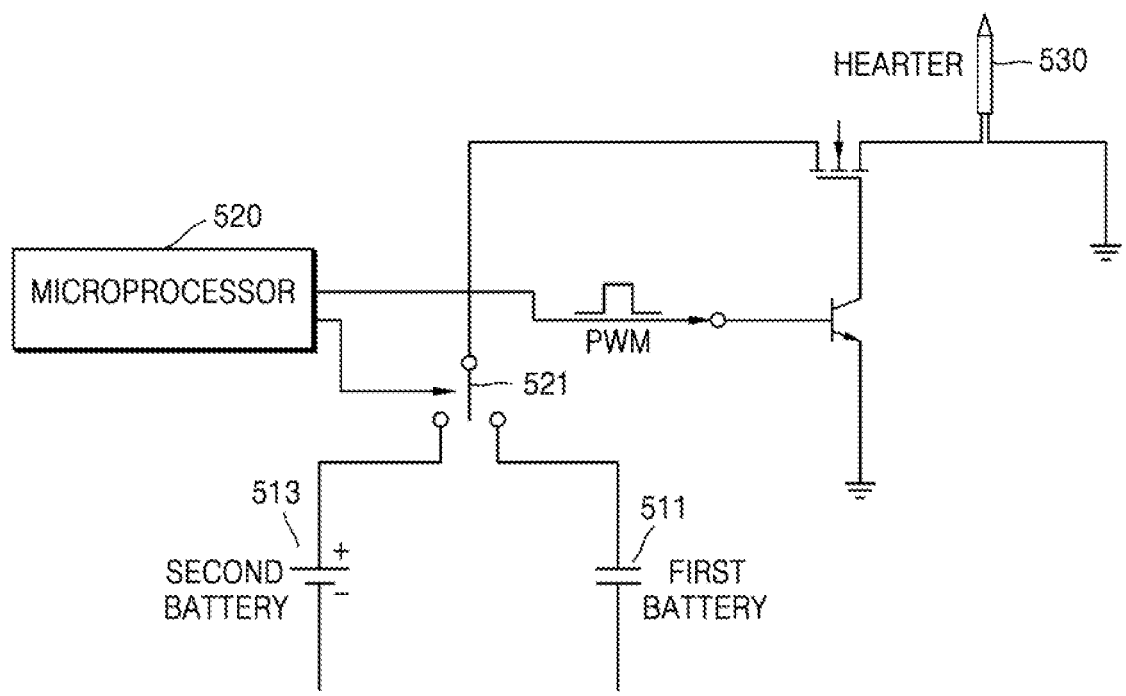
FIG. 5 is a schematic circuit diagram of an aerosol generation device 100 according to an exemplary embodiment.

FIG. 5 is a schematic circuit diagram of an aerosol generation device 100 according to an exemplary embodiment.

Referring to FIG. 5, a first battery 511 or a second battery 513 may be connected to a heater 530 through a switch 521 according to the control by a micro-controller 520. The aerosol generation device 100 may heat the heater 530 by using power supplied from the first battery 511 or the second battery 513.

When controlling the aerosol generation device 100 to operate according to the first mode, the micro-controller 520 may connect the first battery 511 to the heater 530 through the switch 521. In addition, when controlling the aerosol generation device 100 to operate according to the second mode, the micro-controller 520 may connect the second battery 513 to the heater 530 through the switch 521.

In addition, the aerosol generation device 100 may adjust a heating speed of the heater 530 through a PWM signal generated according to the control by the micro-controller 520.

Figure 6:
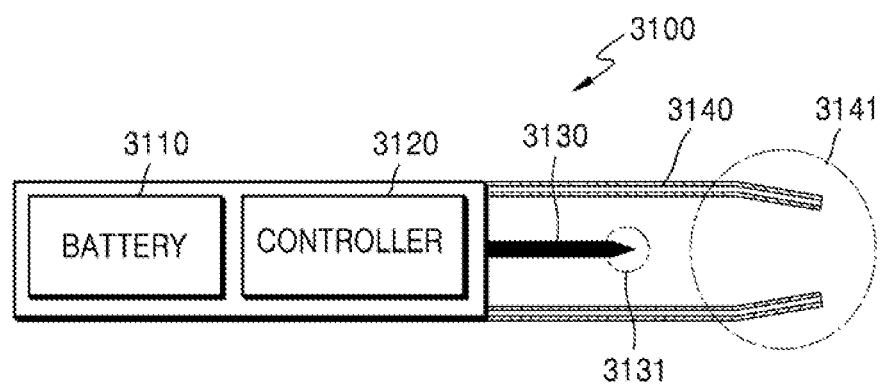
FIG. 6 is a block diagram showing an example of an aerosol generation device.

FIG. 6 is a block diagram showing an example of an aerosol generation device.

Referring to FIG. 6, an aerosol generation device 3100 (hereinafter referred to as a 'holder') includes a battery 3110, a controller 3120, and a heater 3130. The holder 3100 also includes an inner space formed by a casing 3140. A cigarette may be inserted into the inner space of the holder 3100.

Only components associated with the present embodiment are shown in the holder 3100 shown in FIG. 6. Therefore, it will be understood by one of ordinary skill in the art that general components other than the components shown in FIG. 6 may be further included in the holder 3100.

When a cigarette is inserted into the holder 3100, the holder 3100 heats the heater 3130. The temperature of an aerosol generating material in the cigarette is raised by the heated heater 3130, and thus aerosol is generated. The generated aerosol is delivered to a user through a cigarette filter. However, even when a cigarette is not inserted into the holder 3100, the holder 3100 may heat the heater 3130.

The casing 3140 may be detached from the holder 3100. For example, when a user rotates the casing 3140 clockwise or counterclockwise, the casing 3140 may be detached from the holder 3100.

The diameter of a hole formed by a terminal end 3141 of the casing 3140 may be smaller than the diameter of a space formed by the casing 3140 and the heater 3130. In this case, the hole may serve as a guide for a cigarette inserted into the holder 3100.

The battery 3110 supplies power used for the holder 3100 to operate. For example, the battery 3110 may supply power for heating the heater 3130 and supply power for operating the controller 3120. In addition, the battery 3110 may supply power for operating a display, a sensor, a motor, and the like installed in the holder 3100.

The battery 3110 may be a lithium iron phosphate (LiFePO4) battery, but is not limited to the example described above. For example, the battery 3110 may be a lithium cobalt oxide (LiCoO2) battery, a lithium titanate battery, etc.

Also, the battery 3110 may have a cylindrical shape having a diameter of 10 mm and a length of 37 mm, but is not limited thereto. The capacity of the battery 3110 may be 120 mAh or more, and the battery 3110 may be a rechargeable battery or a disposable battery. For example, when the battery 3110 is rechargeable, the charging rate (C-rate) of the battery 3110 may be 10 C and the discharging rate (C-rate) may be 16 C to 20 C. However, the present disclosure is not limited thereto. Also, for stable use, the battery 3110 may be manufactured, such that 80% or more of the total capacity may be ensured even when charging/discharging are performed 8000 times.

Here, it may be determined whether the battery 3110 is fully charged or completely discharged based on a level of power stored in the battery 3110 as compared to the entire capacity of the battery 3110. For example, when power stored in the battery 3110 is equal to or more than 95% of the total capacity, it may be determined that the battery 3110 is fully charged. Furthermore, when power stored in the battery 3110 is 10% or less of the total capacity, it may be determined that the battery 3110 is completely discharged. However, the criteria for determining whether the battery 3110 is fully charged or completely discharged are not limited to the above examples.

The heater 3130 is heated by power supplied from the battery 3110. When a cigarette is inserted into the holder 3100, the heater 3130 is located inside the cigarette. Therefore, the heated heater 3130 may raise the temperature of an aerosol generating material in the cigarette.

The shape of the heater 3130 may be a combination of a cylinderical shape and a conical shape. The diameter of the heater 3130 may be appropriately selected within the range of 2 mm to 3 mm. Preferably, the heater 3130 may be fabricated to have a diameter of 2.15 mm, but is not limited thereto. In addition, the heater 3130 may have a suitable length within the range of 20 mm to 30 mm. Preferably, the heater 3130 may be fabricated to have a length of 19 mm, but is not limited thereto. Also, a terminal end 3131 of the heater 3130 may be formed to have an acute angle, but is not limited thereto. In other words, the heater 3130 may have any shape as long as the heater 3130 may be inserted into the cigarette. In addition, only a portion of the heater 3130 may be heated. For example, assuming that the length of the heater 3130 is 19 mm, only 12 mm from the terminal end 131 of the heater 3130 may be heated, and the remaining portion of the heater 3130 may not be heated.

The heater 3130 may be an electro-resistive heater. For example, the heater 3130 includes an electrically conductive track, and the heater 3130 may be heated as a current flows through the electrically conductive track.

For stable use, the heater 3130 may be supplied with power according to the specifications of 3.2 V, 2.4 A, and 8 W, but is not limited thereto. For example, when power is supplied to the heater 3130, the surface temperature of the heater 3130 may rise to 400° C. or higher. The surface temperature of the heater 3130 may rise to about 350° C. before 15 seconds after the power supply to the heater 3130 starts.

The holder 3100 may be provided with a separate temperature sensor. In another example, the holder 3100 may not be provided with a temperature sensing sensor, and the heater 3130 may serve as a temperature sensing sensor. In another example, the heater 3130 of the holder 3100 may function as a temperature sensor, and the holder 3100 may further include a temperature sensor. For the heater 3130 to function as a temperature sensing sensor, the heater 3130 may include at least one electrically conductive track for heating and temperature sensing. The heater 3130 may further include a second electrically conductive track for temperature sensing in addition to the first electrically conductive track for generating heat.

For example, when a voltage applied to the second electrically conductive track and a current flowing through the second electrically conductive track are measured, a resistance R may be determined. At this time, a temperature T of the second electrically conductive track may be determined by Equation 1 below.

$$R = R_0 \{1 + \alpha(T - T_0)\} \quad \text{[Equation 1]}$$

In Equation 1, R denotes a current resistance value of the second electrically conductive track, $R_0$ denotes a resistance value at a temperature $T_0$ (e.g., 0° C.), and α denotes a resistance temperature coefficient of the second electrically conductive track. Since conductive materials (e.g., metals) have inherent resistance temperature coefficients, α may be determined in advance according to a conductive material constituting the second electrically conductive track. Therefore, when the resistance R of the second electrically conductive track is determined, the temperature T of the second electrically conductive track may be calculated according to Equation 1.

The heater 3130 may include at least one electrically conductive track (a first electrically conductive track and a second electrically conductive track). For example, the heater 3130 may include, but is not limited to, two first electrically conductive tracks and one or two second electrically conductive tracks.

An electrically conductive track includes an electro-resistive material. For example, an electrically conductive track may include a metal. In another example, an electrically conductive track may include an electrically conductive ceramic material, a carbon, a metal alloy, or a composite of a ceramic material and a metal.

In addition, the holder 3100 may include both an electrically conductive track, which serves as a temperature sensing sensor, and a temperature sensing sensor.

The controller 3120 controls the overall operation of the holder 3100. Specifically, the controller 3120 controls not only operations of the battery 3110 and the heater 3130, but also operations of other components included in the holder 3100. The controller 3120 may also check the status of each of the components of the holder 3100 and determine whether the holder 3100 is in an operable state.

The controller 3120 includes at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

For example, the controller 3120 may control the operation of the heater 3130. The controller 3120 may control an amount of power supplied to the heater 3130 and a time for supplying the power, such that the heater 3130 may be heated to a predetermined temperature or maintained at a proper temperature. The controller 3120 may also check the status of the battery 3110 (e.g., the remaining amount of the battery 3110) and generate a notification signal as occasions demand.

Also, the controller 3120 may check the presence or absence of a user's puff, check the strength of the puff, and count the number of puffs. Also, the controller 3120 may continuously check the time during which the holder 3100 is operating. The controller 3120 may also check whether a cradle 3200 to be described below is coupled with the holder 3100 and control the operation of the holder 3100 based on whether the cradle 3200 is coupled with or separated from and the holder 3100.

Meanwhile, the holder 3100 may further include general-purpose components other than the battery 3110, the controller 3120, and the heater 3130.

For example, the holder 3100 may include a display capable of outputting visual information or a motor for outputting tactile information. For example, when a display is included in the holder 3100, the controller 3120 may provide a user information about the state of the holder 3100 (e.g., availability of the holder, etc.), information about the heater 3130 (e.g., start of preheating, progress of preheating, completion of preheating, etc.), information about the battery 3110 (e.g., remaining power of the battery 3110, availability, etc.), information about resetting of the holder 3100 (e.g., reset timing, reset progress, reset completion, etc.), information about cleaning of the holder 3100 (e.g., cleaning timing, need for cleaning, cleaning progress, cleaning completion, etc.), information about charging of the holder 3100 (e.g., need of charging, charging progress, completion of charging, etc.), information about puff (e.g., the number of puffs, notification of expected completion of puffs, etc.), or information about safety (e.g., lapse of time of use, etc.) via the display. In another example, when a motor is included in the holder 3100, the controller 3120 may transmit the above-described information to a user by generating a vibration signal by using the motor.

The holder 3100 may also include a terminal coupled with at least one input device (e.g., a button), through which a user may control the function of the holder 3100, and/or with the cradle 3200. For example, a user may perform various functions by using the input device of the holder 3100. By adjusting the number of times a user presses the input device (e.g., once, twice, etc.) or the time during which the input device is being pressed (e.g., 0.1 second, 0.2 second, etc.), a desired function from among a plurality of functions of the holder 3100 may be executed. As a user manipulates the input device, the holder 3100 may perform a function of preheating the heater 3130, a function of regulating the temperature of the heater 3130, a function of cleaning the space in which a cigarette is inserted, a function of checking whether the battery 3110 is in an operable state, a function of displaying the remaining power (available power) of the battery 3110, a function of resetting the holder 3100, etc. However, the functions of the holder 3100 are not limited to the examples described above.

For example, the holder 3100 may clean the space in which a cigarette is inserted by controlling the heater 3130 as follows. For example, the holder 3100 may clean the space in which a cigarette is inserted by heating the heater 3130 to a sufficiently high temperature. Here, the sufficiently high temperature refers to a temperature suitable for cleaning the space in which a cigarette is inserted. For example, the holder 3100 may heat the heater 3130 to the highest temperature in a temperature range in which an aerosol may be generated from an inserted cigarette and a temperature range for preheating the heater 3130, but the present disclosure is not limited thereto.

In addition, the holder 3100 may maintain the temperature of the heater 3130 at a sufficiently high temperature for a predetermined period of time. Here, the predetermined period of time refers to a period of time sufficient for the space in which a cigarette is inserted to be cleaned. For example, the holder 3100 may maintain the temperature of the heated heater 3130 for a suitable period of time selected within the range of 10 seconds to 10 minutes, but the present disclosure is not limited thereto. Preferably, the holder 3100 may maintain the temperature of the heated heater 3130 for a suitable period of time selected within the range of 20 seconds to 1 minute. More preferably, the holder 3100 may maintain the temperature of the heated heater 3130 for a suitable period of time selected within the range of 20 seconds to 1 minute 30 seconds.

As the holder 3100 heats the heater 3130 to a sufficiently high temperature and also maintains the temperature of the heated heater 3130 for a predetermined period of time, a material deposited on a surface of the heater 3130 and/or the space in which a cigarette is inserted is volatilized, and thus cleaning effect may be obtained.

The holder 3100 may also include a puff detecting sensor, a temperature sensing sensor, and/or a cigarette insertion detecting sensor. For example, the puff detecting sensor may be implemented by a common pressure sensor. Alternatively, the holder 3100 may detect puffs based on a resistance change of an electrically conductive track included in the heater 3130 without a separate puff detecting sensor. Here, the electrically conductive track includes an electrically conductive track for generating heat and/or an electrically conductive track for sensing temperature. Alternatively, the holder 3100 may further include a puff detecting sensor separately from the electrically conductive track included in the heater 3130 and used for detection of puffs.

The cigarette insertion detecting sensor may be implemented by a common capacitive sensor or a resistance sensor. Also, the holder 3100 may be fabricated to have a structure in which the outside air may flow in/out even while the cigarette is inserted.

Figure 7A:
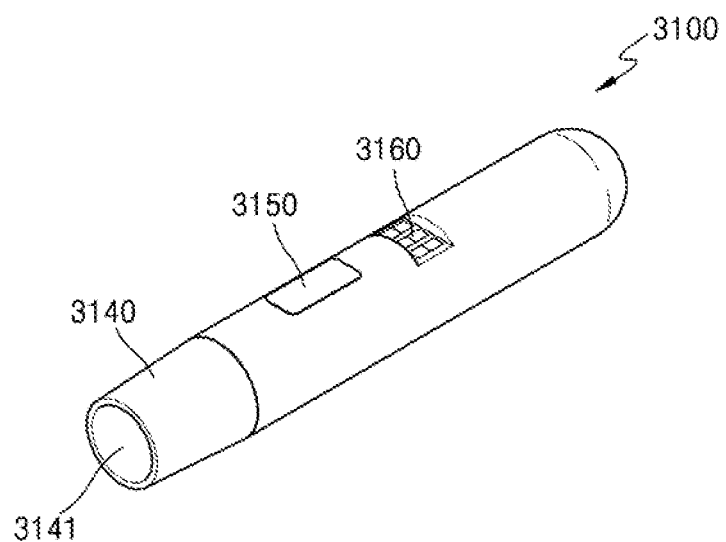
FIGS. 7A and 7B are diagrams showing various views of an example of a holder.
Figure 7B:
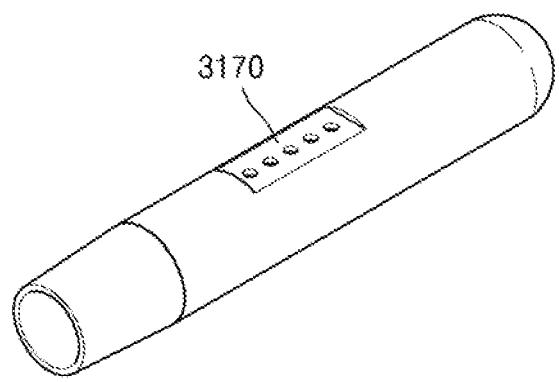

FIGS. 7A and 7B are diagrams showing various views of an example of a holder.

FIG. 7A is a diagram showing an example of the holder 3100 viewed in a first direction. As shown in FIG. 7A, the holder 3100 may be fabricated to have a cylindrical shape, but the present disclosure is not limited thereto. The casing 3140 of the holder 3100 may be separated by an action of a user and a cigarette may be inserted into a terminal end 141 of the casing 3140. The holder 3100 may also include a button 3150 for a user to control the holder 3100 and a display 160 for outputting an image.

FIG. 7B is a diagram showing an example of the holder 3100 viewed in a second direction. The holder 3100 may include a terminal 3170 for coupling with the cradle 3200. As the terminal 3170 of the holder 3100 is coupled with a terminal 3260 of the cradle 3200, the battery 3110 of the holder 3100 may be charged by power supplied by a battery 3210 of the cradle 3200. Also, the holder 3100 may be operated by power supplied from the battery 3210 of the cradle 3200 through the terminal 3170 and the terminal 3260. Also, a communication (transmission/reception of signals) may be performed between the holder 3100 and the cradle 3200 through the terminal 3170 and the terminal 3260. For example, the terminal 3170 may include four micro pins, but the present disclosure is not limited thereto.

Figure 8:
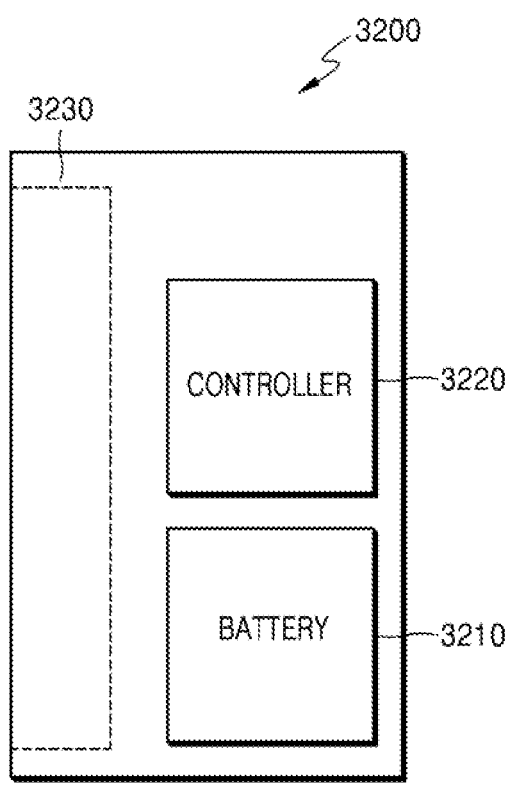
FIG. 8 is a diagram showing an example configuration of a cradle.

FIG. 8 is a diagram showing an example configuration of a cradle.

Referring to FIG. 8, the cradle 3200 includes the battery 3210 and a controller 3220. The cradle 3200 also includes an inner space 3230 into which the holder 3100 may be inserted. For example, the inner space 3230 may be formed on one side of the cradle 3200. Therefore, the holder 3100 may be inserted and fixed in the cradle 3200 even when the cradle 3200 does not include a separate lid.

Only components of the cradle 3200 related to the present embodiment are shown in FIG. 8. Therefore, it will be understood by one of ordinary skill in the art that general-purpose components other than the components shown in FIG. 8 may be further included in the cradle 3200.

The battery 3210 provides power used to operate the cradle 3200. In addition, the battery 3210 may supply power for charging the battery 3110 of the holder 3100. For example, when the holder 3100 is inserted into the cradle 3200 and the terminal 3170 of the holder 3100 is coupled with the terminal 3260 of the cradle 3200, the battery 3210 of the cradle 3200 may supply power to the battery 3110 of the holder 3100.

Also, when the holder 3100 is coupled with the cradle 3200, the battery 3210 may supply power used for the holder 3100 to operate. For example, when the terminal 3170 of the holder 3100 is coupled with the terminal 3260 of the cradle 3200, the holder 3100 may operate by using power supplied by the battery 3210 of the cradle 3200 regardless of whether the battery 3110 of the holder 3100 is discharged or not.

For example, the battery 3210 may be a lithium ion battery, but is not limited thereto. The capacity of the battery 3210 may be greater than the capacity of the battery 3110. For example, the capacity of the battery 3210 may be, but is not limited to, 3000 mAh or greater.

The controller 3220 generally controls the overall operation of the cradle 3200. The controller 3220 may control the overall operation of all the components of the cradle 3200. The controller 3220 may also determine whether the holder 3100 is coupled with the cradle 3200 and control the operation of the cradle 3200 according to coupling or separation of the cradle 3200 and the holder 3100.

For example, when the holder 3100 is coupled with the cradle 3200, the controller 3220 may supply power of the battery 3210 to the holder 3100, thereby charging the battery 3110 or heating the heater 3130. Therefore, even when remaining power of the battery 3110 is low, a user may continuously smoke by coupling the holder 3100 with the cradle 3200.

The controller 3220 includes at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

Meanwhile, the cradle 3200 may further include general-purpose components other than the battery 3210 and the controller 3220. For example, cradle 3200 may include a display capable of outputting visual information. For example, when the cradle 3200 includes a display, the controller 3220 generates a signal to be displayed on the display, thereby informing a user information regarding the battery 3210 (e.g., the remaining power of the battery 3210, availability of the battery 3210, etc.), information regarding resetting of the cradle 3200 (e.g., reset timing, reset progress, reset completion, etc.), information regarding cleaning of the holder 3100 (e.g., cleaning timing, cleaning necessity, cleaning progress, cleaining completion, etc.), information regarding charging of the cradle 3200 (e.g., charging necessity, charging progress, charging completion, etc.).

The cradle 3200 may also include at least one input device (e.g., a button) for a user to control the function of the cradle 3200, a terminal 3260 to be coupled with the holder 3100, and/or an interface for charging the battery 3210 (e.g., an USB port, etc.).

For example, a user may perform various functions by using the input device of the cradle 3200. By controlling the number of times that a user presses the input device or a period of time for which the input device is pressed, a desired function from among the plurality of functions of the cradle 3200 may be executed. As a user manipulates the input device, the cradle 3200 may perform a function of preheating the heater 3130 of the holder 3100, a function of regulating the temperature of the heater 3130 of the holder 3100, a function of cleaning the space in which a cigarette is inserted, a function of checking whether the cradle 3200 is in an operable state, a function of displaying the remaining power (available power) of the battery 3210 of the cradle 3200, a function of resetting the cradle 3200, etc. However, the functions of the cradle 3200 are not limited to the examples described above.

Figure 9A:
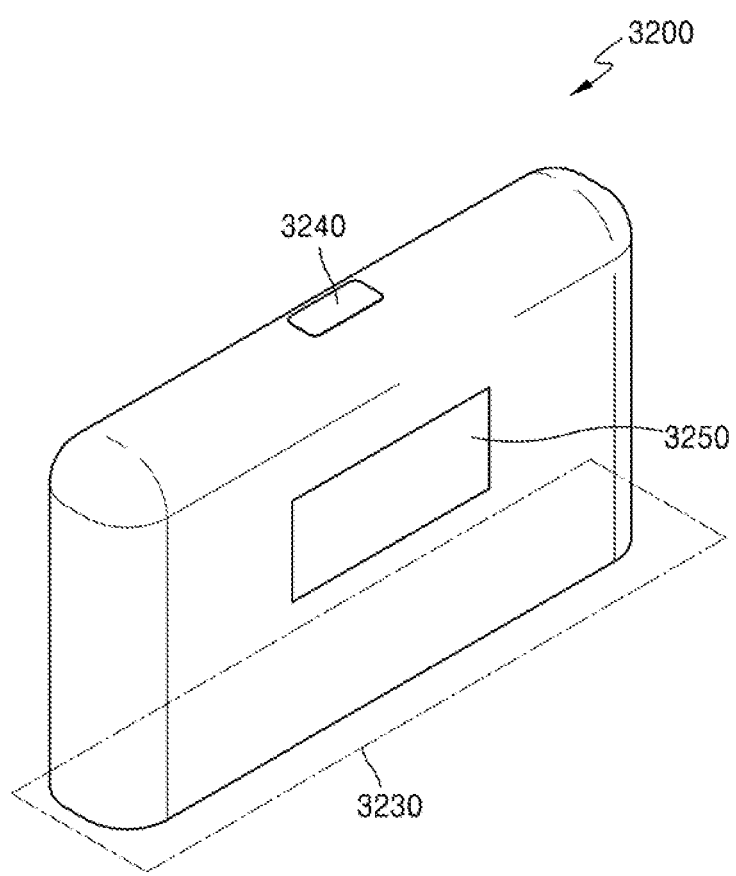
FIGS. 9A and 9B are diagrams showing various views of an example of a cradle.
Figure 9B:
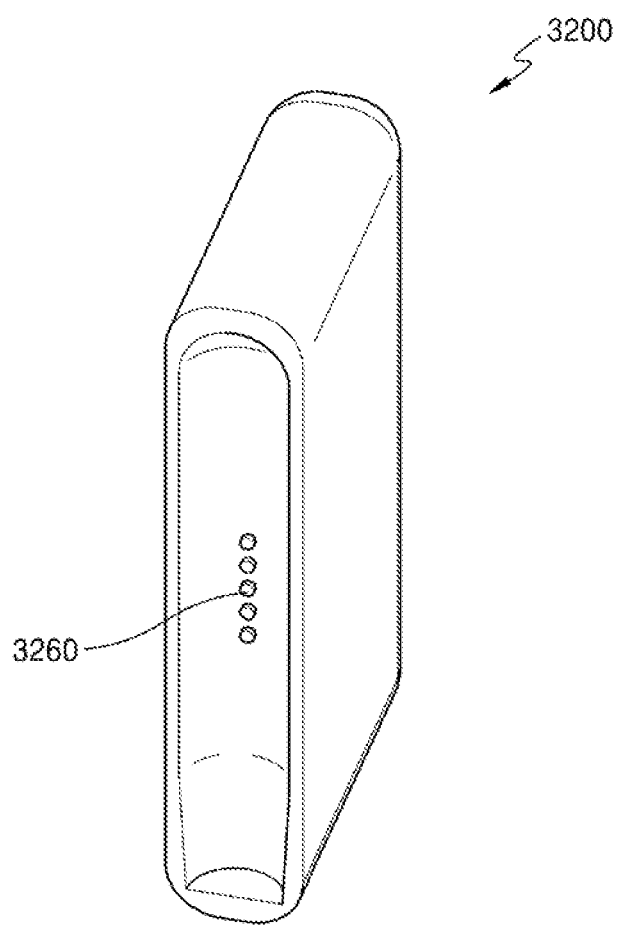

FIGS. 9A and 9B are diagrams showing various views of an example of a cradle.

FIG. 9A is a diagram showing an example of the cradle 3200 viewed in a first direction. The inner space 3230 into which the holder 3100 may be inserted may be formed on one side of the cradle 3200. Also, the holder 3100 may be inserted and fixed in the cradle 3200 even when the cradle 3200 does not include a separate fixing unit like a lid. The cradle 3200 may also include a button 240 for a user to control the cradle 3200 and a display 250 for outputting an image.

FIG. 9B is a diagram showing an example of the cradle 3200 viewed in a second direction. The cradle 3200 may include a terminal 3260 to be coupled with the inserted holder 3100. The battery 3110 of the holder 3100 may be charged by power supplied by the battery 3210 of the cradle 3200 as the terminal 3260 is coupled with the terminal 3170 of the holder 3100. Also, the holder 3100 may be operated by power supplied from the battery 3210 of the cradle 3200 through the terminal 3170 and the terminal 3260. Also, transmission/reception of signals may be performed between the holder 3100 and the cradle 3200 through the terminal 3170 and the terminal 3260. For example, the terminal 3260 may include four micro pins, but the present disclosure is not limited thereto.

The holder 3100 may be inserted into the inner space 3230 of the cradle 3200, as described above with reference to FIGS. 6 to 9B. The holder 3100 may be completely inserted into the cradle 3200 or may be tilted while the holder 3100 is inserted into the cradle 3200. Hereinafter, examples in which the holder 3100 is inserted into the cradle 3200 will be described with reference to FIGS. 10 to 12B.

Figure 10:
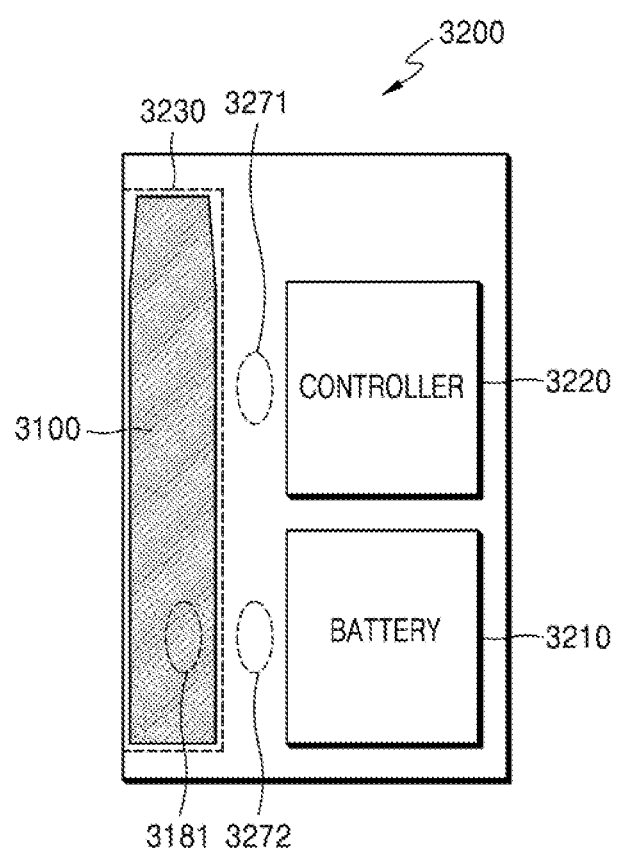
FIG. 10 is a diagram showing an example in which a holder is inserted into a cradle.

FIG. 10 is a diagram showing an example in which a holder is inserted into a cradle.

Referring to FIG. 10, an example in which the holder 3100 is inserted into the cradle 3200 is shown. Since the space 3230 into which the holder 3100 is to be inserted is present on one side surface of the cradle 3200, the inserted holder 3100 may not be exposed to the outside by the other side surfaces of the cradle 3200. Therefore, the cradle 3200 may not include another component (e.g., a lid) for not exposing the holder 3100 to the outside.

The cradle 3200 may include at least one attaching member 3271 and/or 3272 to strengthen the coupling with the holder 3100. Also, at least one attaching member 3181 may be included in the holder 3100 as well. Here, attaching members 3181, 3271, and 3272 may be magnets, but are not limited thereto. Although FIG. 5 shows that the holder 3100 includes one attaching member 181 and the cradle 3200 includes two attaching members 3271 and 3272 for convenience of explanation, the number of the attaching members 3181, 3271, and 3272 is not limited thereto.

The holder 3100 may include the attaching member 181 at a first position and the cradle 3200 may include the attaching members 3271 and 3272 at a second position and a third position, respectively. In this case, the first position and the third position may be facing each other when the holder 3100 is inserted into the cradle 3200.

Since the attaching members 3181, 3271, and 3272 are included in the holder 3100 and the cradle 3200, the holder 3100 and the cradle 3200 may be attached to each other more strongly when the holder 3100 is inserted into one side surface of the cradle 3200. In other words, as the holder 3100 and the cradle 3200 further include the attaching members 3181, 3271, and 3272 in addition to the terminals 3170 and 3260, the holder 3100 and the cradle 3200 may be attached to each other more strongly. Therefore, even when there is no separate component (e.g., a lid) in the cradle 3200, the inserted holder 3100 may not be easily separated from the cradle 3200.

Also, when it is determined that the holder 3100 is completely inserted into the cradle 3200 through the terminals 3170 and 3260 and/or the attaching members 3181, 3271, and 3272, the controller 3220 may charge the battery 3110 of the holder 3100 by using power of the battery 3210.

Figure 11:
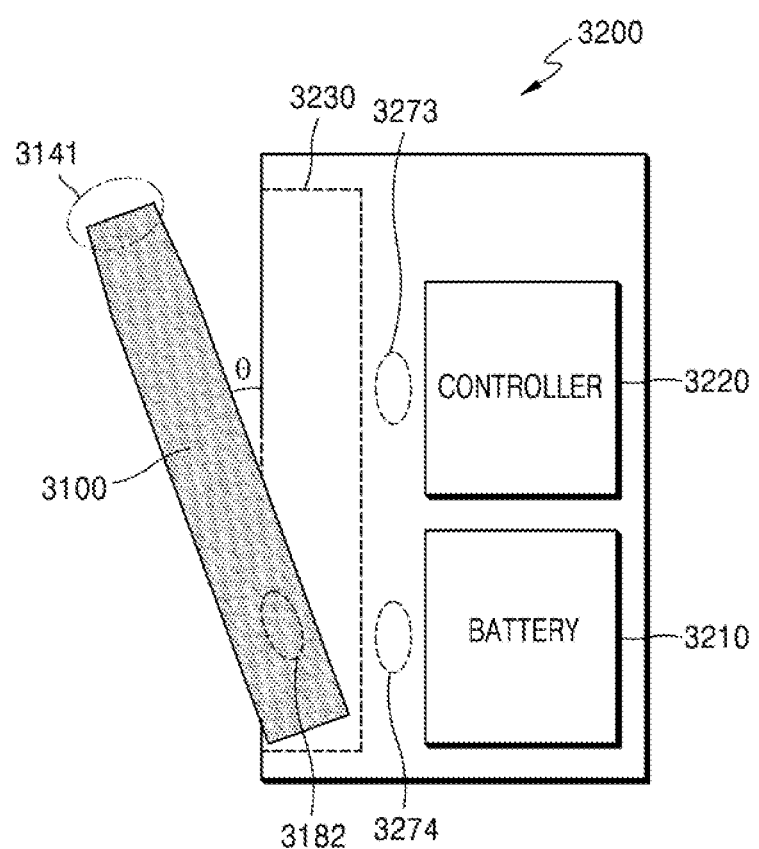
FIG. 11 is a diagram showing an example in which a holder is tilted while being inserted into a cradle.

FIG. 11 is a diagram showing an example in which a holder is tilted while being inserted into a cradle.

Referring to FIG. 11, the holder 3100 is tilted inside the cradle 3200. Here, the term 'tilting' indicates that the holder 3100 is inclined at a certain angle while the holder 3100 is inserted into the cradle 3200.

As shown in FIG. 10, when the holder 3100 is completely inserted into the cradle 3200, a user may not smoke. In other words, once the holder 3100 is completely inserted into the cradle 3200, a cigarette may not be inserted into the holder 3100. Therefore, when the holder 3100 is completely inserted into the cradle 3200, a user may not smoke.

As shown in FIG. 11, when the holder 3100 is tilted, the terminal end 3141 of the holder 3100 is exposed to the outside. Therefore, the user may insert a cigarette into the terminal end 3141 and inhale (smoke) generated aerosol. A sufficient tilting angle θ may be secured to prevent a cigarette from being bent or damaged when the cigarette is inserted into the terminal end 3141 of the holder 3100. For example, the holder 3100 may be tilted at a minimum angle at which an entire cigarette insertion hole included in the terminal end 3141 is exposed to the outside or an angle greater than the minimum angle. For example, the range of the tilting angle θ may be from 0° to 180° and may preferably be from 5° to 90°. More preferably, the range of the tilting angle θ may be from 5° to 20°, from 5° to 30°, from 5° to 40°, from 5° to 50°, or from 5° to 60°. Even more preferably, the tilting angle θ may be 10°.

Also, even when the holder 3100 is tilted, the terminal 3170 of the holder 3100 and the terminal 3260 of the cradle 3200 are still coupled with each other. Therefore, the heater 3130 of the holder 3100 may be heated by power supplied by the battery 3210 of the cradle 3200. Therefore, the holder 3100 may generate aerosol by using the battery 3210 of the cradle 3200 even when the remaining power of the battery 3110 of the holder 3100 is low or the battery 3110 of the holder 3100 is completely discharged.

FIG. 11 shows an example in which the holder 3100 includes one attaching member 3182 and the cradle 3200 includes two attaching members 3273 and 3274. For example, the respective positions of the attaching members 3182, 3273, and 3274 are as described above with reference to FIG. 10. Assuming that the attaching members 3182, 3273, and 3274 are magnets, the magnetic strength of the attaching member 3274 may be greater than the magnetic strength of the attaching member 3273. Therefore, the holder 3100 may not be completely separated from the cradle 3200 due to the attaching member 182 and the attaching member 274 even when the holder 3100 is tilted.

Also, when it is determined that the holder 3100 titled through the terminals 3170 and 3260 and/or the attaching members 3181, 3271, and 3272, the controller 3220 may heat the heater 3130 of the holder 3100 or charge the battery 3110, by using power of the battery 3210.

Figure 12A:
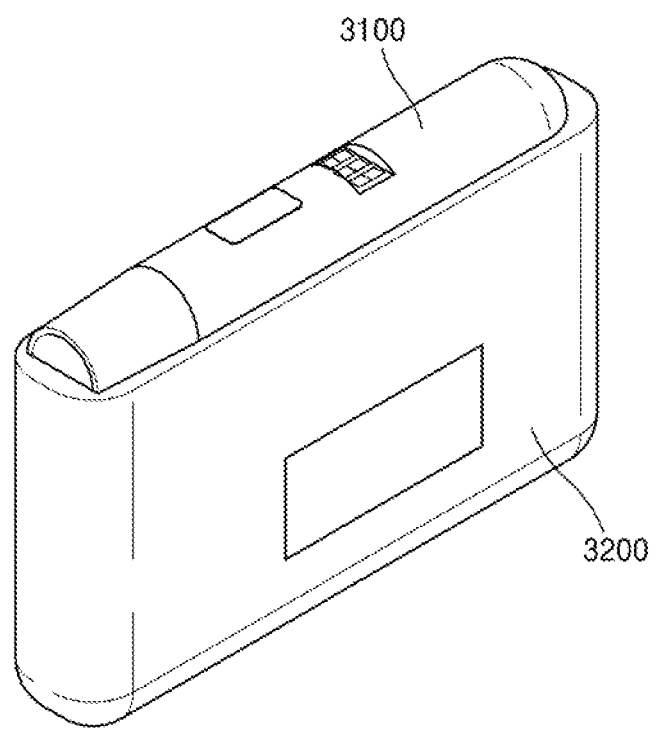
FIGS. 12A to 12B are diagrams showing examples in which a holder is inserted into a cradle.
Figure 12B:
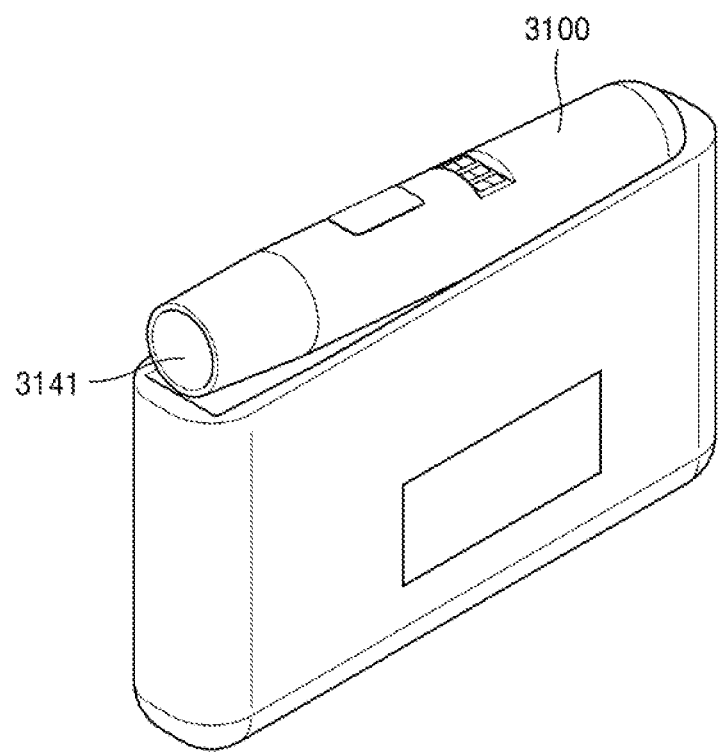

FIGS. 12A to 12B are diagrams showing examples in which a holder is inserted into a cradle.

FIG. 12A shows an example in which the holder 3100 is completely inserted into the cradle 3200. The cradle 3200 may be fabricated to provide the sufficient inner space 3230 of the cradle 3200 to minimize the contact of a user with the holder 3100 when the holder 3100 is completely inserted into the cradle 3200. When the holder 3100 is completely inserted into the cradle 3200, the controller 3220 supplies power of the battery 3210 to the holder 3100, such that the battery 3110 of the holder 3100 is charged.

FIG. 12B shows an example in which the holder 3100 is tilted while being inserted into the cradle 3200. When the holder 3100 is tilted, the controller 3220 supplies power of the battery 3210 to the holder 3100, such that the battery 3110 of the holder 3100 is charged or the heater 3130 of the holder 3100 is heated.

Figure 13:
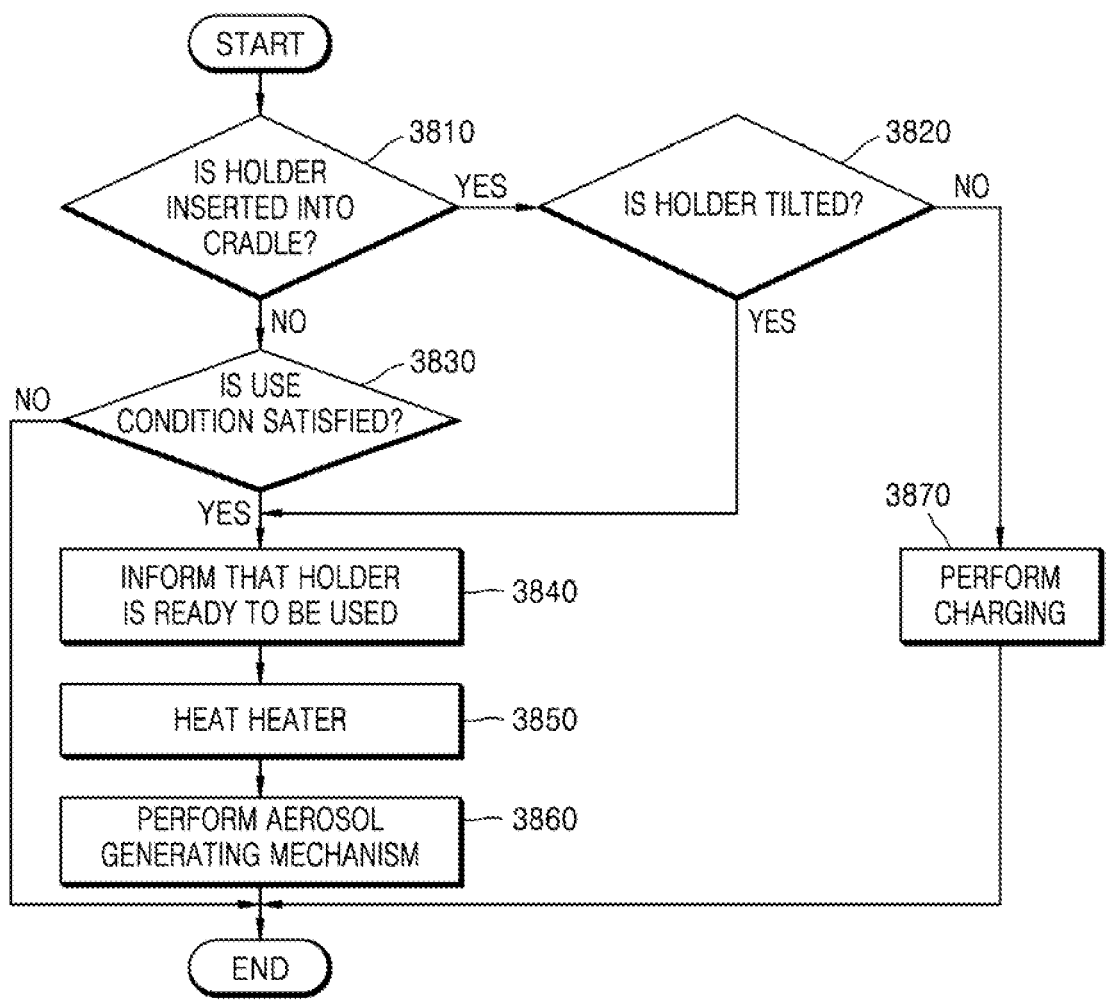
FIG. 13 is a flowchart for describing an example in which a holder and a cradle operates.

FIG. 13 is a flowchart for describing an example in which a holder and a cradle operates.

A method for generating aerosol shown in FIG. 13 includes operations that are performed in a time-series manner by the holder 3100 or the cradle 3200 shown in FIG. 6 or 8. Therefore, it will be understood that the descriptions given above with respect to the holder 3100 and the cradle 3200 shown in FIG. 6 or 8 also apply to the method of FIG. 13, even when the descriptions are omitted below.

In operation 3810, the holder 3100 determines whether it is inserted in the cradle 3200. For example, the controller

3120 may determine whether the holder 3100 is inserted into the cradle 3200 based on whether the terminals 3170 and 3260 of the holder 3100 and the cradle 3200 are connected to each other and/or whether the attaching members 3181, 3271, and 3272 are operating.

When the holder 3100 is inserted into the cradle 3200, the method proceeds to operation 3820. When the holder 3100 is separated from the cradle 3200, the method proceeds to operation 3830.

In operation 3820, the cradle 3200 determines whether the holder 3100 is tilted. For example, the controller 3220 may determine whether the holder 3100 is inserted into the cradle 3200 based on whether the terminals 3170 and 3260 of the holder 3100 and the cradle 3200 are connected to each other and/or whether attaching members 3182, 3273, and 3274 are operating.

Although it is described that the cradle 3200 determines whether the holder 3100 is tilted in operation 3820, the present disclosure is not limited thereto. In other words, the controller 3120 of the holder 3100 may determine whether the holder 3100 is tilted.

When the holder 3100 is tilted, the method proceeds to operation 3840. When the holder 3100 is not tilted (i.e., the holder 3100 is completely inserted into the cradle 3200), the method proceeds to operation 3870.

In operation 3830, the holder 3100 determines whether conditions of using the holder 3100 are satisfied. For example, the controller 3120 may determine whether the conditions for using the holder 3100 are satisfied by checking whether the remaining power of the battery 3110 and whether other components of the holder 3100 may be normally operated.

When the conditions for using the holder 3100 are satisfied, the method proceeds to operation 3840. Otherwise, the procedure is terminated.

In operation 3840, the holder 3100 informs a user that the holder 3100 is ready to be used. For example, the controller 3120 may output an image indicating that the holder 3100 is ready to be used, on the display of the holder 3100, or may control the motor of the holder 3100 to generate a vibration signal.

In operation 3850, the heater 3130 is heated. For example, when the holder 3100 is separated from the cradle 3200, the heater 3130 may be heated by power of the battery 3110 of the holder 3100. In another example, when the holder 3100 is tilted, the heater 3130 may be heated by power of the battery 3210 of the cradle 3200.

The controller 3120 of the holder 3100 or the controller 3220 of the cradle 3200 may check the temperature of the heater 3130 in real time and control an amount of power supplied to the heater 3130 and a time for supplying the power to the heater 3130. For example, the controller 3120 or 3220 may check the temperature of the heater 3130 in real time through a temperature sensor included in the holder 3100 or an electrically conductive track of the heater 3130.

In operation 3860, the holder 3100 performs an aerosol generation mechanism. For example, the controller 3120, 3220 may check the temperature of the heater 3130, which changes as a user performs puffs, and adjust an amount of power supplied to the heater 3130 or stop supplying power to the heater 3130. Also, the controller 3120 or 3220 may count the number of puffs of the user and output information indicating that the holder 3100 needs to be cleaned when the number of puffs reaches a certain number of times (e.g., 1500 times).

In operation 3870, the cradle 3200 performs charging of the holder 3100. For example, the controller 3220 may charge the holder 3100 by supplying power of the battery 3210 of the cradle 3200 to the battery 3110 of the holder 3100.

Meanwhile, the controller 3120 or 3220 may stop the operation of the holder 3100 according to the number of puffs of the user or the operation time of the holder 3100. Hereinafter, an example in which the controller 3120 or 3220 stops the operation of the holder 3100 will be described with reference to FIG. 14.

Figure 14:
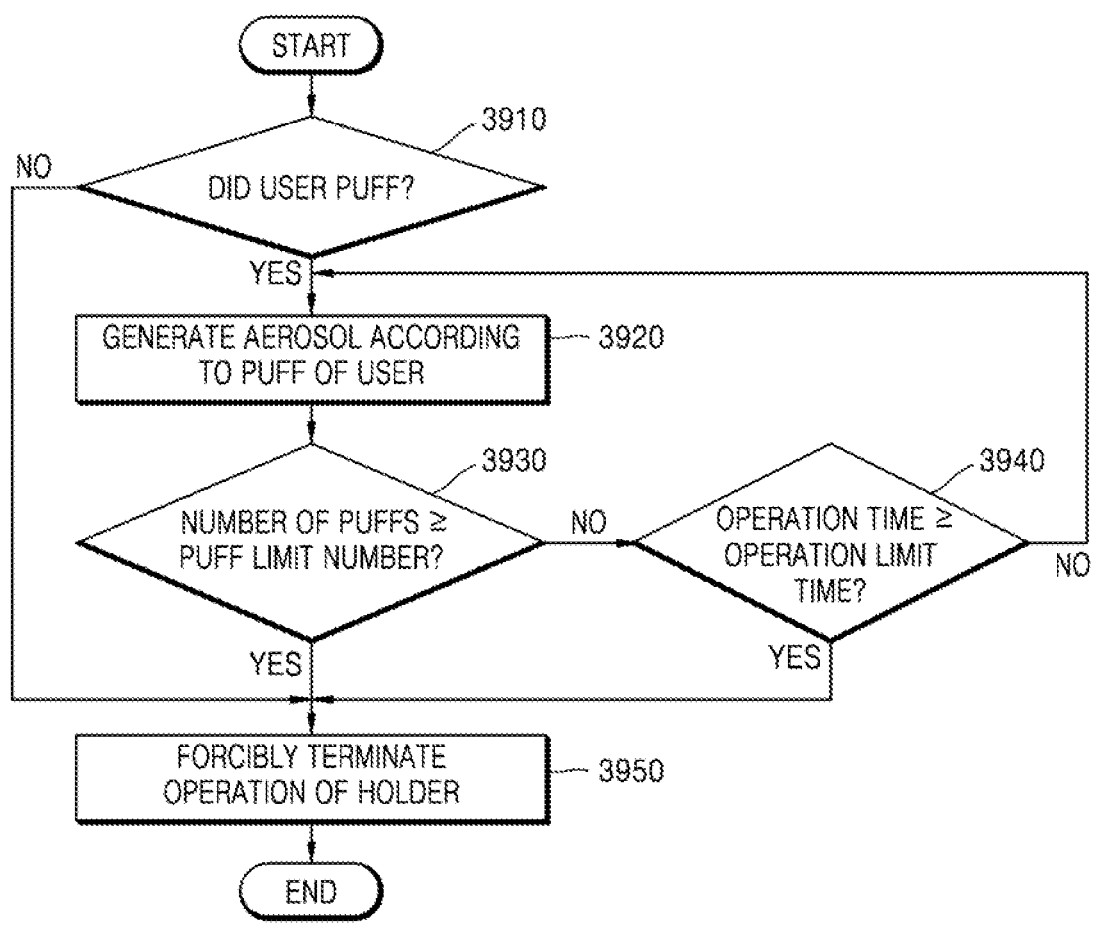
FIG. 14 is a flowchart for describing an example in which a holder operates.

FIG. 14 is a flowchart for describing an example in which a holder operates.

A method for generating aerosols shown in FIG. 14 includes operations that are performed in a time-series manner by the holder 3100 and the cradle 3200 shown in FIG. 6 or 8. Therefore, it will be understood that the descriptions given above with respect to the holder 3100 and the cradle 3200 shown in FIG. 6 or 8 also apply to the method of FIG. 14, even when the descriptions are omitted below.

In operation 3910, the controller 3120 or 3220 determines whether a user puffed. For example, the controller 3120 or 3220 may determine, through the puff detecting sensor included in the holder 3100, whether the user puffed. Alternatively, the controller 3120 or 3220 may determine whether the user puffed, by using the resistance change of the electrically conductive track included in the heater 3130. Here, the electrically conductive track includes an electrically conductive track for generating heat and/or an electrically conductive track for sensing temperature. Alternatively, the controller 3120 or 3220 may determine whether the user puffed, by using both the resistance change of the electrically conductive track included in the heater 3130 and the puff detecting sensor.

In operation 3920, aerosol is generated according to the puff of the user. The controller 3120 or 3220 may adjust power supplied to the heater 3130 according to the puff of the user the temperature of the heater 3130, as described above with reference to FIG. 13. Also, the controller 3120 or 3220 counts the number of puffs of the user.

In operation 3930, the controller 3120 or 3220 determines whether the number of puffs of the user equal to or greater than a puff limit number. For example, assuming that the puff limit number is set to 14, the controller 3120 or 3220 determines whether the number of counted puffs is 14 or more. However, the puff limit number is not limited to 14. For example, the puff limit number may be set to an appropriate number of times selected in the range of 10 to 16.

On the other hand, when the number of puffs of the user is close to the puff limit number (e.g., when the number of puffs of the user is 12), the controller 3120 or 3220 may output a warning signal through a display or a vibration motor.

When the number of puffs of the user is equal to or greater than the puff limit number, the method proceeds to operation 3950. When the number of puffs of the user is less than the puff limit number, the method proceeds to operation 3940.

In operation 3940, the controller 3120 or 3220 determines whether the operation time of the holder 3100 is equal to or greater than an operation limit time. Here, the operation time of the holder 3100 refers to accumulated time from a time point at which the holder 3100 started its operation to a current time point. For example, assuming that the operation limit time is set to 10 minutes, the controller 3120 or 4220 determines whether the holder 3100 is operating for 10 minutes or longer.

On the other hand, when the operation time of the holder 3100 is close to the operation limit time (e.g., when the holder 3100 is operating for 8 minutes), the controller 3120 or 3220 may output a warning signal through a display or a vibration motor.

When the holder 3100 is operating for the operation limit time or longer, the method proceeds to operation 3950. When the operation time of the holder 3100 is less than the operation limit time, the method proceeds to operation 3920.

In operation 3950, the controller 3120 or 3220 forcibly terminates the operation of the holder 3100. In other words, the controller 3120 or 3220 terminates the aerosol generation mechanism of the holder 3100. For example, the controller 3120 or 3220 may forcibly terminate the operation of the holder 3100 by interrupting the power supplied to the heater 3130.

Figure 15:
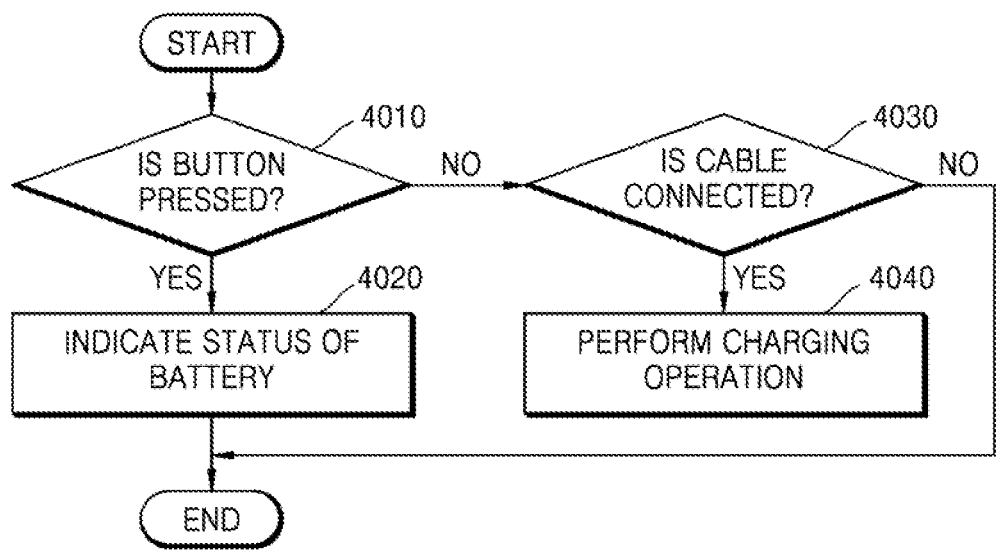
FIG. 15 is a flowchart for describing an example in which a cradle operates.

FIG. 15 is a flowchart for illustrating operations of a cradle, according to an exemplary embodiment.

The flowchart shown in FIG. 15 includes operations that are performed in a time-series manner by the cradle 3200 shown in FIG. 8. Therefore, it will be understood that the descriptions given above with respect to the cradle 3200 shown in FIG. 8 also apply to the method of FIG. 15, even when the descriptions are omitted below.

Although not shown in FIG. 15, the operation of the cradle 3200 to be described below may be performed regardless of whether the holder 3100 is inserted into the cradle 3200.

In operation 4010, the controller 3220 of the cradle 3200 determines whether the button 3240 is pressed. When the button 3240 is pressed, the method proceeds to operation 4020. When the button 3240 is not pressed, the method proceeds to operation 4030.

In operation 4020, the cradle 3200 indicates the status of the battery 3210. For example, the controller 3220 may output information regarding the current state of the battery 3210 (e.g., remaining power, etc.) on the display 3250.

In operation 4030, the controller 3220 of the cradle 3200 determines whether a cable is connected to the cradle 3200. For example, the controller 3220 determines whether a cable is connected to an interface (e.g., a USB port, etc.) included in the cradle 3200. When a cable is connected to the cradle 3200, the method proceeds to operation 4040. Otherwise, the procedure is terminated.

In operation 4040, the cradle 3200 performs a charging operation. For example, the cradle 3200 charges the battery 3210 by using power supplied through a connected cable.

As described above with reference to FIG. 6, a cigarette may be inserted into the holder 3100. The cigarette includes an aerosol generating material and aerosol is generated by the heated heater 3130.

Hereinafter, an example of a cigarette that can be inserted into the holder 3100 will be described with reference to FIGS. 16 to 18F.

Figure 16:
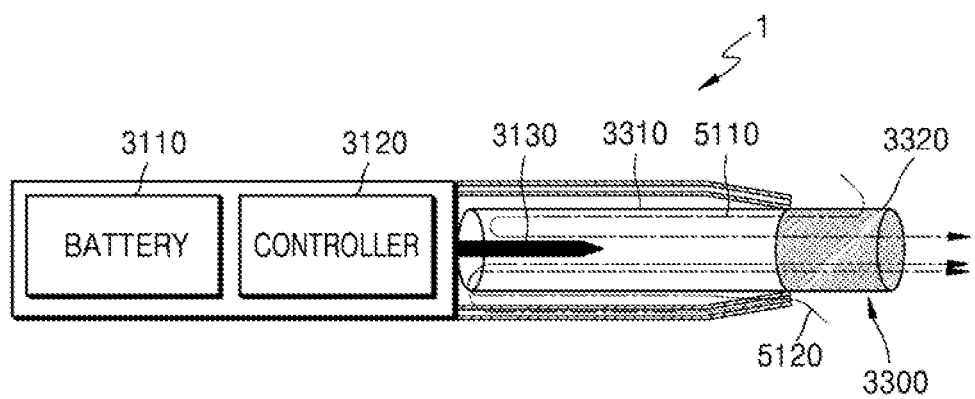
FIG. 16 is a diagram showing an example in which a cigarette is inserted into a holder.

FIG. 16 is a diagram showing an example in which a cigarette is inserted into a holder.

Referring to FIG. 16, the cigarette 3300 may be inserted into the holder 3100 through the terminal end 3141 of the casing 3140. When the cigarette 3300 is inserted into the holder 3100, the heater 3130 is located inside the cigarette 3300. Therefore, the heated heater 3130 heats the aerosol generating material of the cigarette 3300, thereby generating aerosol.

The cigarette 3300 may be similar to a typical combustive cigarette. For example, the cigarette 3300 may include a first portion 3310 containing an aerosol generating material and a second portion 3320 including a filter and the like.

Meanwhile, the cigarette 3300 according to an exemplary embodiment may also include an aerosol generating material in the second portion 3320. For example, an aerosol generating material in the form of granules or capsules may be inserted into the second portion 3320.

The entire first portion 3310 may be inserted into the holder 3100 and the second portion 3320 may be exposed to the outside. In another example, only a portion of the first portion 3310 may be inserted into the holder 3100. In another example, the entire first portion 3310 and a portion the second portion 3320 may be inserted into the holder 3100.

A user may inhale the aerosol while holding the second portion 3320 by mouth. At this time, the aerosol is generated as the outside air passes through the first portion 3310, and the generated aerosol passes through the second portion and is delivered to a user's mouth.

The outside air 5120 may be introduced through at least one air passage formed in the holder 3100. For example, opening and closing of the air passage formed in the holder 3100 and/or the size of the air passage may be adjusted by a user. Accordingly, an amount of smoke and a smoking impression may be adjusted by the user.

Alternatively, the outside air 5110 may be introduced through at least one hole formed in the surface of the cigarette 3300.

Figure 17A:
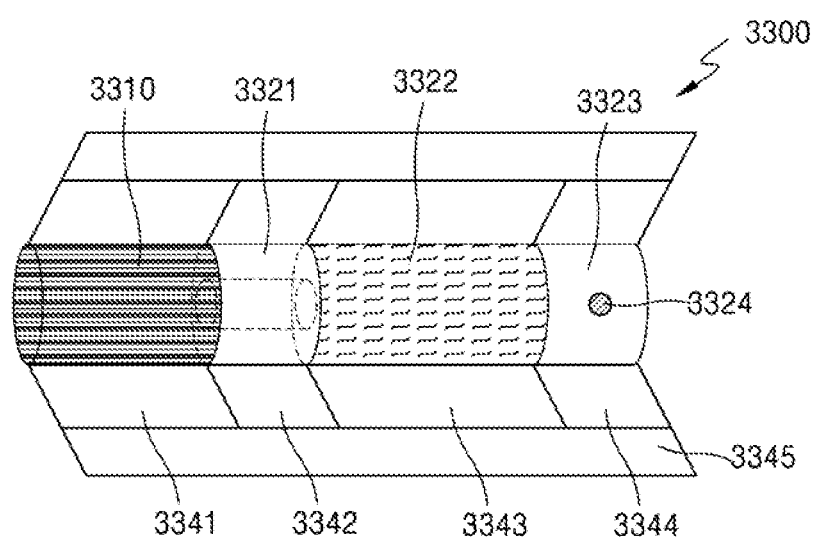
FIGS. 17A and 17B are block diagrams showing examples of a cigarette.
Figure 17B:
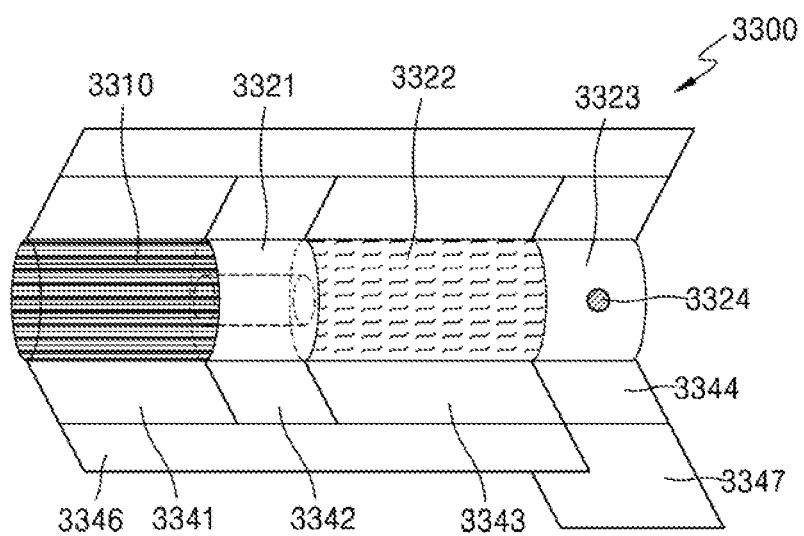

FIGS. 17A and 17B are block diagrams showing examples of a cigarette.

Referring to FIGS. 17A and 17B, the cigarette 3300 includes a tobacco rod 3310, a first filter segment 3321, a cooling structure 3322, and a second filter segment 3323. The first portion 3310 described above with reference to FIG. 16 includes the tobacco rod 3310, and the second portion 3320 includes the first filter segment 3321, the cooling structure 3322, and the second filter segment 3323.

Referring to FIG. 17A, the cigarette 3300 may be packaged by a total of five wrappers 3341, 3342, 3343, 3344, and 3345. Meanwhile, referring to FIG. 17B, the cigarette 3300 may be packaged by a total of six wrappers 3341, 3342, 3343, 3344, 3346 and 3347. The tobacco rod 3310 is packed by a first wrapper 3341, and the first filter segment 3321 is packaged by a second wrapper 3342. Also, the cooling structure 3322 is packed by a third wrapper 3343, and the second filter segment 3323 is packed by a fourth wrapper 3344.

A fifth wrapper 3345 of FIG. 17A may be wrapped around the first wrapper 3341, the second wrapper 3342, the third wrapper 3343, and the fourth wrapper 3344. In other words, the entire cigarette 3300 may be double-packaged by the fifth wrapper 3345.

On the other hand, a sixth wrapper 3346 of FIG. 17B may be wrapped around the first wrapper 3341, the second wrapper 3342, and the third wrapper 3343. In other words, the tobacco rod 3310, the first filter segment 3321, and the cooling structure 3322 of the cigarette 3300 may be double-packaged by the sixth wrapper 3346. Also, a seventh wrapper 3347 of FIG. 17B may be wrapped around at least a portion of the third wrapper 3343 and the fourth wrapper 3344. In other words, at least a portion of the cooling structure 3322 and the second filter segment 3323 of the cigarette 3300 may be re-packaged by the seventh wrapper 3347.

The first wrapper 3341 and the second wrapper 3342 may be fabricated using a general filter wrapping paper. For example, the first wrapper 3341 and the second wrapper 3342 may include a porous wrapping paper or a non-porous wrapping paper. Also, the first wrapper 3341 and the second wrapper 3342 may be made of an oil-resistant paper sheet and an aluminum laminate packaging material.

The third wrapper 3343 may be made of a hard wrapping paper. For example, the basis weight of the third wrapper 3343 may be, but is not limited to, 90 g/m².

The fourth wrapper 3344 may be made of an oil-resistant hard wrapping paper. For example, the basis weight of the fourth wrapper 3344 may be 92 g/m² and the thickness thereof may be 125 μm, but the present disclosure is not limited thereto.

The fifth wrapper 3345, the sixth wrapper 3346, and the seventh wrapper 3347 may be made of a sterilized paper (MFW). Here, the MFW refers to a paper specially manufactured to have the tensile strength, the water resistance, the smoothness, and the like that are improved compared to those of ordinary paper. For example, the basis weight of the fifth wrapper 3345, the sixth wrapper 3346, and the seventh wrapper 3347 may be 60 g/m² and the thickness thereof may be 67 m, but the present disclosure is not limited thereto. Also, the tensile strengths of the fifth wrapper 3345, the sixth wrapper 3346, and the seventh wrapper 3347 may be within the range of 8 kgf/15 mm to 11 kgf/15 mm for dry type and may be 1.0 kgf/15 mm for wet type, but the present disclosure is not limited thereto.

A predetermined material may be included in the fifth wrapper 3345, the sixth wrapper 3346, and the seventh wrapper 3347. Here, an example of the predetermined material may be, but is not limited to, silicon. For example, silicon exhibits characteristics like heat resistance with little change due to the temperature, oxidation resistance, resistances to various chemicals, water repellency, electrical insulation, etc. However, any material other than silicon may be applied to (or coated on) the fifth wrapper 3345, the sixth wrapper 3346, and the seventh wrapper 3347 without limitation as long as the material exhibits the above-mentioned characteristics.

The fifth wrapper 3345, the sixth wrapper 3346, and the seventh wrapper 3347 may prevent the cigarette 3300 from being burned. For example, when the tobacco rod 3310 is heated by the heater 3130, there is a possibility that the cigarette 3300 is burned. In detail, when the temperature is raised to a temperature above the ignition point of any one of materials included in the tobacco rod 3310, the cigarette 3300 may be burned. Even in this case, since the fifth wrapper 3345, the sixth wrapper 3346, and the seventh wrapper 3347 include a non-combustible material, the burning of the cigarette 3300 may be prevented.

Furthermore, the fifth wrapper 3345, the sixth wrapper 3346, and the seventh wrapper 3347 may prevent the holder 3100 from being contaminated by substances formed by the cigarette 3300. Through puffs of a user, liquid substances may be formed in the cigarette 3300. For example, as the aerosol generated by the cigarette 3300 is cooled by the outside air, liquid materials (e.g., moisture, etc.) may be formed. As the fifth wrapper 3345, the sixth wrapper 3346, and the seventh wrapper 3347 wrap the tobacco rod 3310 and/or the first filter segment 3321, the liquid materials formed in the cigarette 3300 may be prevented from being leaked out of the cigarette 3300. Accordingly, the casing 3140 of the holder 3100 and the like may be prevented from being contaminated by the liquid materials formed by the cigarette 3300.

The diameter of the cigarette 3300 may be within the range of 5 mm to 9 mm, and the length thereof may be about 48 mm. However, the present disclosure is not limited thereto. Preferably, the diameter of the cigarette 3300 may be 7.2 mm, but is not limited thereto. In addition, the length of the tobacco rod 3310 may be about 12 mm, the length of the first filter segment 3321 may be about 10 mm, the length of the cooling structure 3322 may be about 14 mm, and the length of the second filter segment 3323 may be about 12 mm, but the present disclosure is not limited thereto.

The structures of the cigarette 3300 shown in FIGS. 17A and 17B are merely examples, and some of the components may be omitted. For example, the cigarette 3300 may not include one or more of the first filter segment 3321, the cooling structure 3322, and the second filter segment 3323.

The tobacco rod 3310 includes an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol.

In addition, the tobacco rod 3310 may include other additive materials like a flavoring agent, a wetting agent, and/or an organic acid. For example, the flavoring agent may include licorice, sucrose, fructose syrup, isosweet, cocoa, lavender, cinnamon, cardamom, celery, fenugreek, cascara, sandalwood, bergamot, geranium, honey essence, rose oil, vanilla, lemon oil, orange oil, mint oil, cinnamon, keragene, cognac, jasmine, chamomile, menthol, cinnamon, ylang ylang, salvia, spearmint, ginger, coriander, coffee, etc. In addition, the wetting agent may include glycerin or propylene glycol.

For example, the tobacco rod 3310 may be filled with cut tobacco leaves. Here, cut tobacco leaves may be formed by fine-cutting a tobacco sheet.

For a large wide tobacco sheet to be filled within the tobacco rod 3310 having a narrow space, a special operation for facilitating folding of the tobacco sheet is further needed. Therefore, it is easier to fill the tobacco rod 3310 with cut tobacco leaves compared to filling the tobacco rod 3310 with a tobacco sheet, and thus the productivity and the efficiency of the process for producing the tobacco rod 3310 may be improved.

In another example, the tobacco rod 3310 may be filled with a plurality of cigarette strands formed by fine-cutting a tobacco sheet. For example, the tobacco rod 3310 may be formed by combining a plurality of tobacco strands in the same direction (parallel to one another) or randomly. In detail, the tobacco rod 3310 may be formed by combining a plurality of tobacco strands, and a plurality of vertical channels through which the heater 3130 may be inserted or aerosol may pass may be formed. At this time, depending on the sizes and arrangements of the tobacco strands, the vertical channels may be uniform or non-uniform.

For example, tobacco strands may be formed through the following operations. First, a raw tobacco material is pulverized to form a slurry in which an aerosol generating material (e.g., glycerin, propylene glycol, etc.), a flavoring liquid, a binder (e.g., guar gum, xanthan gum, carboxymethyl cellulose (CMC), etc.), and water are mixed, and then a sheet is formed by using the slurry. When forming the slurry, natural pulp or cellulose may be added to modify the physical properties of tobacco strands, and one or more binders may be mixed and used. Next, after drying the sheet, tobacco strands may be formed by fold-cutting or fine-cutting the dried sheet.

The raw tobacco material may be tobacco leaf fragments, tobacco stems, and/or fine tobacco powders formed during treatment of tobacco. The tobacco sheet may also include other additives like wood cellulose fibers.

The slurry may contain 5% to 40% aerosol generating material, and 2% to 35% aerosol generating material may remain in completed tobacco strands. Preferably, 10% to 25% of the aerosol generating material may remain in the completed tobacco strands.

Also, before the tobacco rod 3310 is packaged by the first wrapper 3341, a flavoring liquid like a menthol or a moisturizer may be spray-added to the center of the tobacco rod 3310.

The tobacco strands may be fabricated to have cuboidal shapes having horizontal lengths from 0.5 mm to 2 mm, vertical lengths from 5 mm to 50 mm, and thicknesses (heights) from 0.1 mm to 0.3 mm, but the present disclosure is not limited thereto. Preferably, the tobacco strands may be fabricated to have a cuboidal shape having the horizontal length of 0.9 mm, the vertical length of 20 mm, and the thickness (height) of 0.2 mm. Also, one tobacco strand may be fabricated to have a basis weight from 100 $g/m^2$ to 250 $g/m^2$, but the present disclosure is not limited thereto. Preferably, one tobacco strand may be fabricated to have a basis weight of 180 $g/m^2$.

Compared with the tobacco rod 3310 filled with a cigarette sheet, the tobacco rod 3310 filled with tobacco strands may generate a greater amount of aerosol. In the case of filling the same space, compared to a tobacco sheet, tobacco strands ensure a wider surface area. A wider surface area indicates that an aerosol generating material has a greater chance of contacting the outside air. Therefore, when the tobacco rod 3310 is filled with tobacco strands, more aerosol may be generated when compared with the tobacco rod 3310 filled with a tobacco sheet.

Furthermore, when the cigarette 3300 is separated from the holder 3100, the tobacco rod 3310 filled with tobacco strands may be separated more easily than the tobacco rod 3310 filled with a tobacco sheet. In other words, when the tobacco rod 3310 is filled with tobacco strands, the tobacco rod 3310 may be more easily separated from the holder 3100 than the tobacco sheet 310 filled with a tobacco sheet.

The first filter segment 3321 may be a cellulose acetate filter. For example, the first filter segment 3321 may have a tubular structure including a hollow therein. The length of the first filter segment 3321 may be any suitable length within the range of 4 mm to 30 mm, but is not limited thereto. Preferably, the length of the first filter segment 3321 may be 10 mm, but is not limited thereto.

The diameter of the hollow included in the first filter segment 3321 may be any suitable diameter within the range of 3 mm to 4.5 mm, but is not limited thereto.

The hardness of the first filter segment 3321 may be adjusted by adjusting the content of a plasticizer during fabrication of the first filter segment 3321.

To prevent the size of the first filter segment 3321 from decreasing over time, the first filter segment 3321 may be wrapped by a wrapper. Therefore, the first filter segment 3321 may be easily combined with other components (e.g., other filter segments).

Also, the first filter segment 3321 may be fabricated by inserting structures of the same type or different types like films or tubes thereinto (e.g., into the hollow).

The first filter segment 3321 may be fabricated using cellulose acetate. Therefore, the inner material of the tobacco rod 3310 may be prevented from being pushed back when the heater 3130 is inserted, and the effect of cooling an aerosol may occur.

The cooling structure 3322 cools aerosol generated as the heater 3130 heats the tobacco rod 3310. Therefore, a user may inhale aerosol cooled to a suitable temperature.

The length or the diameter of the cooling structure 3322 may vary depending on the shape of the cigarette 3300. For example, the length of the cooling structure 3322 may be suitably selected within the range of 7 mm to 20 mm. Preferably, the length of the cooling structure 3322 may be about 14 mm, but is not limited thereto.

The cooling structure 3322 may be made of pure polylactic acid or may be made of a combination of other degradable polymers and polylactic acid. For example, the cooling structure 3322 may be manufactured by an extrusion method or a weaving method of fibers. The cooling structure 3322 can be manufactured in various forms to increase the surface area (i.e., surface area in contact with the aerosol) per unit area.

For example, the cooling structure 3322 can be made by weaving fibers made of polylactic acid. In this case, a fragrance liquid may be applied to the fibers made of polylactic acid. Alternatively, the cooling structure 3322 may be manufactured by using fibers applied to the fragrance liquid and fibers made of polylactic acid. In addition, the polylactic acid fibers may be dyed in a predetermined color, and a cooling structure 3322 may be manufactured using the dyed fibers.

Various examples of the cooling structure 3322 are described below with reference to FIGS. 18A to 18F.

The second filter segment 3323 may also be a cellulose acetate filter. For example, the second filter segment 3323 may be fabricated as a recess filter, but is not limited thereto. The length of the second filter segment 3323 may be appropriately selected within the range of 4 mm to 20 mm. For example, the length of the second filter segment 3323 may be about 12 mm, but is not limited thereto.

The second filter segment 3323 may be fabricated to generate a flavor by spraying a flavoring liquid to the second filter segment 3323 during fabrication of the second filter segment 3323. Alternatively, separate fibers coated with a flavoring liquid may be inserted into the second filter segment 3323. Aerosol formed in the tobacco rod 3310 is cooled as it passes through the cooling structure 3322, and the cooled aerosol is delivered to a user through the second filter segment 3323. Therefore, when a flavoring material is added to the second filter segment 3323, the effect of enhancing the persistence of a flavor delivered to the user may occur.

Also, the second filter segment 3323 may include at least one capsule 3324. Here, the capsule 3324 may have a structure in which a content liquid containing a flavoring material is wrapped with a film. For example, the capsule 3324 may have a spherical or cylindrical shape.

The film of the capsule 3324 may be fabricated by using a material including agar, pectin, sodium alginate, carrageenan, gelatin, or a gum like guar gum. Furthermore, a gelling agent may be further used as a material for forming the film of the capsule 3324. Here, as the gelling agent, for example, a calcium chloride group may be used. Furthermore, a plasticizer may be further used as a material for forming the film of the capsule 3324. As the plasticizer, glycerin and/or sorbitol may be used. Furthermore, a coloring agent may be further used as a material for forming the film of the capsule 3324.

For example, as a flavoring material included in the content liquid of the capsule 3324, menthol, plant essential oil, and the like may be used. As a solvent of the flavoring material included in the content liquid, for example, a medium chain fatty acid triglyceride (MCT) may be used. Also, the content liquid may include other additives like a figment, an emulsifying agent, a thickening agent, etc.

FIGS. 18A to 18F are diagrams for describing an example of a cooling structure of a cigarette.

For example, the cooling structure shown in FIGS. 18A to 18F can be manufactured using fibers produced from pure polylactic acid (PLA).

As an example, when the film (sheet) is filled to produce a cooling structure for the film (sheet), the film (sheet) may be broken by an external impact. In this case, the cooling effect of the cooling structure is reduced.

As another example, when manufacturing a cooling structure by extrusion molding or the like, as the process of cutting the structure is added, the efficiency of the process is lowered. There is also a limitation in manufacturing the cooling structure in various shapes.

By manufacturing (eg, weaving) a cooling structure using polylactic acid fibers according to an exemplary embodiment, the risk that the cooling structure is deformed or damaged by external impacts can be lowered. In addition, by changing the manner of combining the fibers, it is possible to produce a cooling structure having a variety of shapes.

In addition, by making the cooling structure with the fibers, the surface area in contact with the aerosol is increased. Thus, the cooling effect of the cooling structure can be further improved.

Figure 18A:
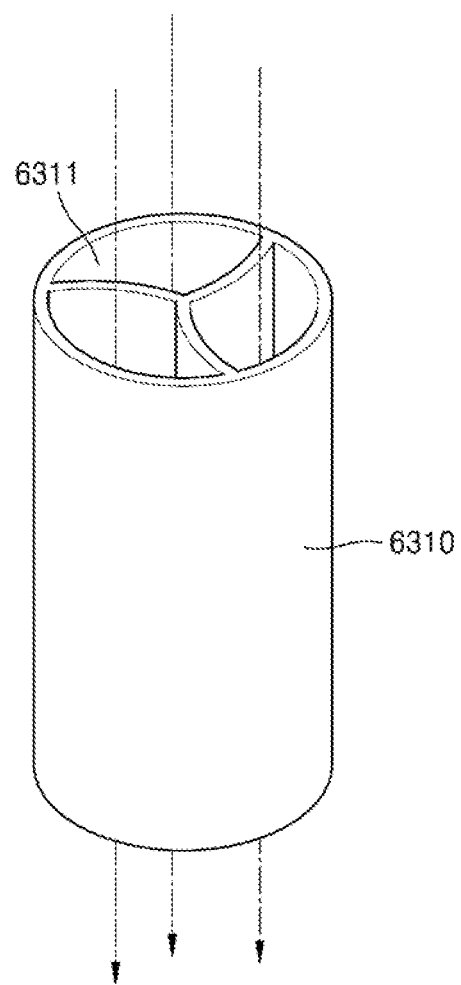
FIGS. 18A to 18F are diagrams for describing an example of a cooling structure of a cigarette.

Referring to FIG. 18A, the cooling structure 6310 may be manufactured in a cylindrical shape, and at least one air passage 6311 may be formed in a cross section of the cooling structure 6310.

Figure 18B:
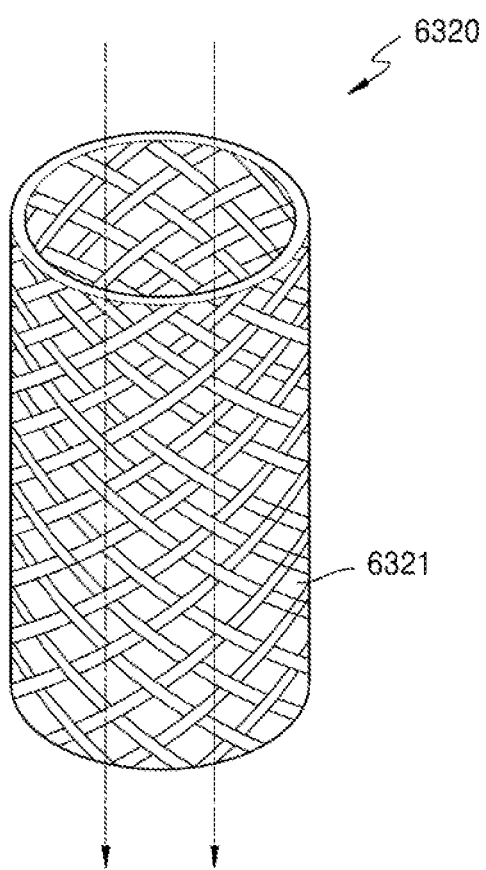

Referring to FIG. 18B, the cooling structure 6320 may be manufactured as a structure in which a plurality of fibers are entangled with each other. In this case, the aerosol may flow between the fibers, and vortex may be formed according to the shape of the cooling structure 6320. The vortex formed widens the area that aerosol contacts in the cooling structure 6320 and increases the time the aerosol stays in the cooling structure 6320. Thus, the heated aerosol can be cooled effectively.

Figure 18C:
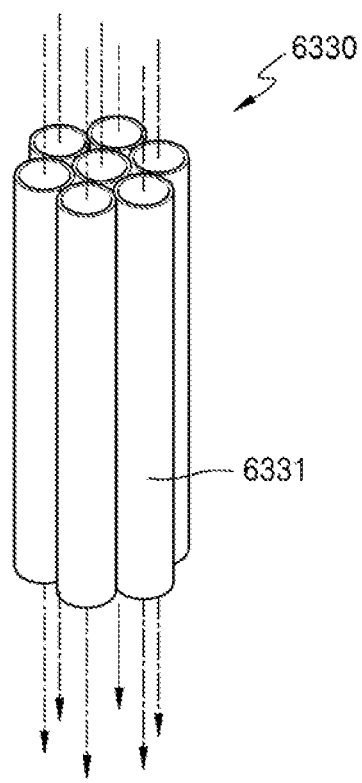

Referring to FIG. 18C, the cooling structure 6330 may be manufactured in the form of a plurality of bundles 6321.

Figure 18D:
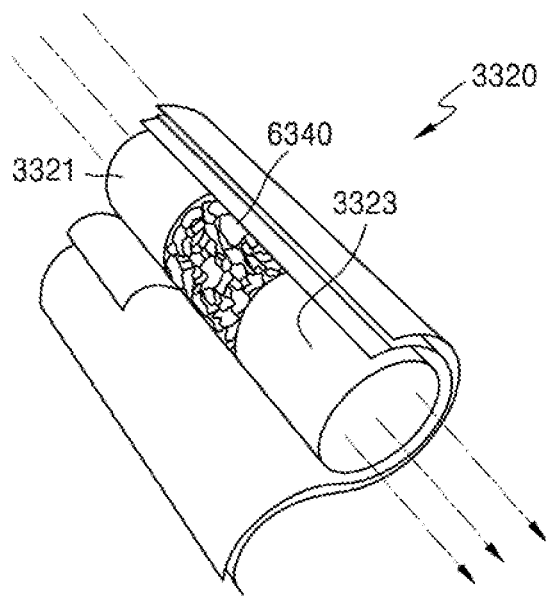

Referring to FIG. 18D, the cooling structure 6340 may be filled with granules made of polylactic acid, vinegar or charcoal, respectively. Granules may also be prepared from a mixture of polylactic acid, vinegar and charcoal. On the other hand, the granules may further include elements capable of increasing the cooling effect of the aerosol in addition to polylactic acid, vinegar and/or charcoal.

Figure 18E:
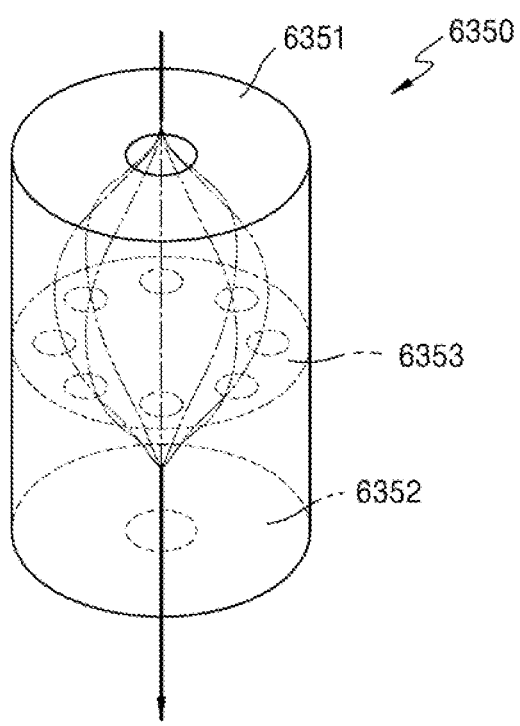

Referring to FIG. 18E, the cooling structure 6350 may include a first cross-section 6351 and a second cross-section 6352.

The first cross section 6351 borders the first filter segment 3321 and may include a void into which the aerosol flows. The second cross section 6352 borders the second filter segment 3323 and may include a void through which the aerosol may be released. For example, the first cross-section 6351 and the second cross-section 6352 may include a single void having the same diameter, but the diameter and number of the voids included in the first cross-section 6351 and the second cross-section 6352 is not limited thereto.

In addition, the cooling structure 6350 may include a third cross section 6353 including a plurality of voids between the first cross section 6351 and the second cross section 6352. For example, the diameters of the plurality of voids included in the third cross section 6535 may be smaller than the diameters of the voids included in the first cross section 6351 and the second cross section 6352. In addition, the number of voids included in the third cross section 6353 may be greater than the number of voids included in the first cross section 6351 and the second cross section 6352.

Figure 18F:
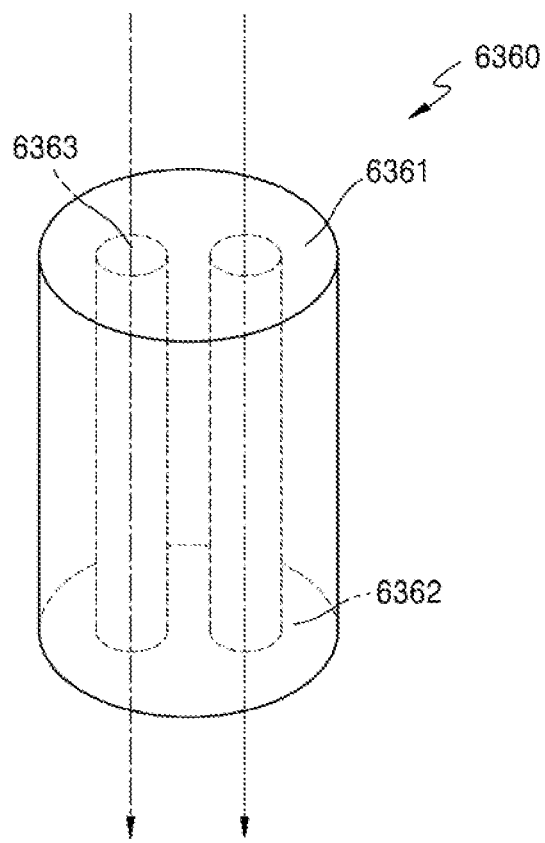

Referring to FIG. 18F, the cooling structure 6360 may include a first cross section 6361 bordering the first filter segment 3321 and a second cross section 6362 bordering the second filter segment 3323. In addition, cooling structure 6360 may include one or more tubular elements 6363. For example, the tubular element 6363 can penetrate the first cross section 6361 and the second cross section 6362. In addition, the tubular element 6363 may be packaged in a microporous package and filled with a filler (e.g., the granules described above with reference to FIG. 18D) that may increase the cooling effect of the aerosol.

According to the above, the holder can generate aerosol by heating the cigarette. It is also possible to produce aerosol either independently from the holder or while the holder inserted into the cradle and tilted. In particular, when the holder is tilted, the heater may be heated by the power of the battery of the cradle.

On the other hand, the above-described method can be written as a program that can be executed in a computer, it can be implemented in a general-purpose digital computer to operate the program using a computer-readable recording medium. In addition, the structure of the data used in the above-described method can be recorded on the computer-readable recording medium through various means. The computer-readable recording medium may include a storage medium such as a magnetic storage medium (e.g., ROM, RAM, USB, floppy disk, hard disk, etc.), an optical reading medium (e.g., CD-ROM, DVD, etc.).

Those skilled in the art will appreciate that the present invention may be embodied in a modified form without departing from the essential characteristics of the above-described substrate. Therefore, the aforementioned exemplary embodiments should be considered in a descriptive sense only and not for purposes of limitation. The scope of the present invention is shown in the claims rather than the foregoing description, and all differences within the scope will be construed as being included in the present invention.

The invention claimed is:

1. An aerosol generation device comprising:
   a power supplier comprising a first power supply device and a second power supply device;
   a heater; and
   a controller configured to:
   control the power supplier to operate according to one of a first mode in which the first power supply device supplies power to the heater and a second mode in which the second power supply device supplies power to the heater, and
   control the power supplier to supply greater power in the first mode than in the second mode,
   wherein the first power supply device has greater C-rate than the second power supply device such that the first power supply device is charged or discharged faster than the second power supply device.

2. The aerosol generation device of claim 1, wherein the first mode is a mode for raising a temperature of the heater, and the second mode is a mode for maintaining the temperature of the heater.

3. The aerosol generation device of claim 1, wherein the first power supply device comprises a lithium-ion capacitor.

4. The aerosol generation device of claim 1, wherein the second power supply device comprises one of a lithium-ion cell battery, a lithium iron phosphate battery, a lithium-titanate battery, and a lithium polymer battery.

5. The aerosol generation device of claim 1, further comprising a sensor for sensing inhalation by a user, wherein, upon sensing the inhalation, the controller controls the power supplier to operate according to the first mode.

6. The aerosol generation device of claim 1, further comprising:
   a sensor for sensing inhalation by a user; and
   a sensor for measuring a temperature of the heater,
   wherein, upon sensing the inhalation, the controller controls the power supplier to operate according to the first mode when the temperature of the heater is equal to or lower than a first temperature, and controls the power supplier to operate according to the second mode when the temperature of the heater is higher than the first temperature.

7. The aerosol generation device of claim 1, wherein the controller is configured to:
   control the power supplier to operate according to the first mode while a temperature of the heater is raised to a threshold temperature, and
   when the temperature of the heater reaches the threshold temperature or higher, control the power supplier to operate according to the second mode.

8. The aerosol generation device of claim 1, wherein the controller is configured to:
   control the power supplier to operate according to the first mode for a first period, and
   when the first period ends, control the power supplier to operate according to the second mode.

9. The aerosol generation device of claim 1, further comprising:
   a memory storing a condition under which the first mode is switched to the second mode,
   wherein the condition comprises a temperature of the heater and a period of time during which the power supplier is operated according to the first mode.

10. A control method for an aerosol generation device, the method comprising:
    when inhalation by a user is sensed and a temperature of a heater is equal to or lower than a first temperature, controlling a power supplier to operate according to a first mode in which the power supplier supplies power to the heater from a first power supply device; and
    controlling the power supplier to operate according to one of the first mode and a second mode, based on the temperature of the heater or a period of time during which the power supplier is operated according to the first mode,
    wherein power is supplied to the heater from a second power supply device in the second mode,
    wherein the power supplier supplies greater power to the heater in the first mode than in the second mode,
    wherein the first power supply device and the second power supply device are included in the aerosol generation device, and
    wherein the first power supply device has greater C-rate than the second power supply device such that the first power supply device is charged or discharged faster than the second power supply device.

11. The control method of claim 10, wherein
    the first mode is a mode for raising the temperature of the heater, and the second mode is a mode for maintaining the temperature of the heater.

12. The control method of claim 10, wherein
    the first power supply device comprises a lithium-ion capacitor.

13. The control method of claim 10, wherein
    the second power supply device comprises one of a lithium-ion cell battery, a lithium iron phosphate battery, a lithium-titanate battery, and a lithium polymer battery.

14. The control method of claim 10, further comprising:
    controlling the power supplier to operate according to the second mode when the inhalation is sensed and the temperature of the heater exceeds the first temperature.

15. The control method of claim 10, further comprising:
    controlling the power supplier to operate according to the first mode while the temperature of the heater is raised to a threshold temperature; and
    controlling the power supplier to operate according to the second mode when the temperature of the heater is equal to or higher than the threshold temperature.

16. The control method of claim 10, further comprising:
    controlling the power supplier to operate according to the first mode for a first period; and
    controlling the power supplier to operate according to the second mode when the first period ends.

* * * * *